United States Patent
Goldfine et al.

(10) Patent No.: US 7,526,964 B2
(45) Date of Patent: May 5, 2009

(54) APPLIED AND RESIDUAL STRESS MEASUREMENTS USING MAGNETIC FIELD SENSORS

(75) Inventors: Neil J. Goldfine, Newton, MA (US); Vladimir A. Zilberstein, Chestnut Hill, MA (US); James M. Fisher, Centerville, GA (US); David C. Grundy, Reading, MA (US); Darrell E. Schlicker, Watertown, MA (US); Vladimir Tsukernik, West Roxbury, MA (US); Robert J. Lyons, Boston, MA (US); Ian C. Shay, Cambridge, MA (US); Andrew P. Washabaugh, Chula Vista, CA (US)

(73) Assignee: JENTEK Sensors, Inc., Waltham, MA (US)

( * ) Notice: Subject to any disclaimer, the term of this patent is extended or adjusted under 35 U.S.C. 154(b) by 0 days.

(21) Appl. No.: 10/351,978

(22) Filed: Jan. 24, 2003

(65) Prior Publication Data

US 2003/0173958 A1 Sep. 18, 2003

Related U.S. Application Data

(60) Provisional application No. 60/351,666, filed on Jan. 25, 2002.

(51) Int. Cl.
*G01N 3/32* (2006.01)
(52) U.S. Cl. ..................................................... 73/779
(58) Field of Classification Search .................. 73/779, 73/761, 597, 601, 627, 767, 582, 861.21; 324/232, 235, 242, 230, 220, 238, 209, 219, 324/262, 225; 422/82.08; 81/470, 57.38
See application file for complete search history.

(56) References Cited

U.S. PATENT DOCUMENTS

| | | | | |
|---|---|---|---|---|
| 3,665,756 A | * | 5/1972 | Russell | 73/766 |
| 3,977,236 A | * | 8/1976 | Raatz et al. | 73/614 |
| 4,095,181 A | * | 6/1978 | Harris et al. | 324/238 |
| 4,142,154 A | * | 2/1979 | Couchman | 324/219 |
| 4,203,069 A | * | 5/1980 | Davis | 324/220 |
| 4,247,819 A | * | 1/1981 | Shimada et al. | 324/233 |
| 4,383,218 A | * | 5/1983 | Hansen et al. | 324/225 |
| 4,454,790 A | * | 6/1984 | Rieben | 73/761 |

(Continued)

OTHER PUBLICATIONS

Auld, B.A. and Moulder, J.C. (1999), "Review of Advances in Quantitative Eddy-Current Nondestructive Evaluation," Journal of Nondestructive Evaluation, vol. 18, No. 1.

(Continued)

*Primary Examiner*—Harshad Patel
*Assistant Examiner*—Octavia Davis
(74) *Attorney, Agent, or Firm*—Hamilton, Brook, Smith and Reynolds, P.C.

(57) ABSTRACT

Methods are described for the use of conformable eddy-current sensors and sensor arrays for characterizing residual stresses and applied loads in materials. In addition, for magnetizable materials such as steels, these methods can be used to determine carbide content and to inspect for grinding burn damage. The sensor arrays can be mounted inside or scanned across the inner surface of test articles and hollow fasteners to monitor stress distributions. A technique for placing eddy-current coils around magnetizable fasteners for load distribution monitoring is also disclosed.

23 Claims, 19 Drawing Sheets

U.S. PATENT DOCUMENTS

| | | | | |
|---|---|---|---|---|
| 4,528,856 | A | * | 7/1985 | Junker et al. .................. 73/779 |
| 4,706,020 | A | | 11/1987 | Viertl et al. |
| 4,814,690 | A | | 3/1989 | Melcher et al. |
| 4,823,606 | A | * | 4/1989 | Malicki ....................... 73/761 |
| 4,846,001 | A | * | 7/1989 | Kibblewhite ................ 73/761 |
| 5,015,951 | A | | 5/1991 | Melcher |
| 5,023,549 | A | * | 6/1991 | Dau et al. .................... 324/220 |
| 5,047,719 | A | * | 9/1991 | Johnson et al. ............. 324/242 |
| 5,156,636 | A | * | 10/1992 | Kuljis ......................... 73/597 |
| 5,291,789 | A | * | 3/1994 | Walton ....................... 73/761 |
| 5,399,968 | A | * | 3/1995 | Sheppard et al. ............ 324/242 |
| 5,453,689 | A | | 9/1995 | Goldfine et al. |
| 5,499,540 | A | * | 3/1996 | Whaley et al. ............... 73/761 |
| 5,510,709 | A | * | 4/1996 | Hurley et al. ............... 324/242 |
| 5,549,803 | A | * | 8/1996 | Schoess et al. .............. 204/404 |
| 5,610,515 | A | * | 3/1997 | Soules ........................ 324/209 |
| 5,648,721 | A | | 7/1997 | Wincheski et al. |
| 5,675,087 | A | * | 10/1997 | MacLauchlan et al. ........ 73/761 |
| 5,739,686 | A | * | 4/1998 | Naughton et al. ........... 324/259 |
| 5,793,206 | A | | 8/1998 | Goldfine et al. |
| RE36,986 | E | | 12/2000 | Melcher |
| 6,188,218 | B1 | | 2/2001 | Goldfine et al. |
| 6,380,747 | B1 | | 4/2002 | Goldfine et al. |
| 6,479,989 | B2 | * | 11/2002 | Taylor ....................... 324/219 |
| 6,486,673 | B1 | | 11/2002 | Goldfine et al. |
| 6,545,469 | B1 | * | 4/2003 | Batzinger et al. ........... 324/238 |
| 6,657,429 | B1 | | 12/2003 | Goldfine et al. |
| 6,727,690 | B2 | * | 4/2004 | Soules ........................ 324/209 |
| 6,727,691 | B2 | * | 4/2004 | Goldfine et al. ............. 324/240 |
| 6,781,387 | B2 | | 8/2004 | Goldfine et al. |
| 6,784,662 | B2 | * | 8/2004 | Schlicker et al. ............ 324/242 |
| 6,888,346 | B2 | | 5/2005 | Wincheski et al. |
| 6,952,095 | B1 | * | 10/2005 | Goldfine et al. ............. 324/240 |
| 6,992,482 | B2 | * | 1/2006 | Shay et al. .................. 324/235 |
| 2001/0054896 | A1 | | 12/2001 | Mednikov et al. |
| 2002/0075006 | A1 | | 6/2002 | Goldfine et al. |
| 2002/0163333 | A1 | | 11/2002 | Schlicker et al. |
| 2003/0071614 | A1 | | 4/2003 | Buttle |
| 2003/0071615 | A1 | | 4/2003 | Schlicker et al. |
| 2003/0173958 | A1 | | 9/2003 | Goldfine et al. |
| 2004/0100277 | A1 | | 5/2004 | Tam |
| 2004/0124833 | A1 | | 7/2004 | Kliman et al. |
| 2005/0007106 | A1 | | 1/2005 | Goldfine et al. |
| 2005/0083032 | A1 | | 4/2005 | Goldfine et al. |
| 2007/0007955 | A1 | | 1/2007 | Goldfine et al. |
| 2008/0258720 | A1 | | 10/2008 | Goldfine et al. |

OTHER PUBLICATIONS

Bozorth, R.M., Ferromagnetism, IEEE Press, 1978.
Bray, D.E., ed., Residual Stress Measurement and General Nondestructive Evaluation, PVP-vol. 429, ASME Pressure Vessels and Piping Conference, Atlanta, GA, ASME, 2001.
Hydrogen in Metals, Proceedings of the Second Japan Institute of Metals, International Symposium, 1979.
Interrante, C. and Pressouyre, G. "Current Solutions to Hydrogen Problems in Steels," Proceedings of the First International Conference, ASM, 1982.
Lawrence, S.C. "Hydrogen Detection Gage," Hydrogen Embrittlement Testing, ASTM STP 543, 1974, pp. 83-105.
Navy Phase I Proposal, titled "Wireless Communications with Electromagnetic Sensor Networks for Nondestructive Evaluation," Topic #N01-174, dated Aug. 13, 2001.
Air Force Phase I Proposal, titled "Three-Dimensional Magnetic Imaging of Damage in Multiple Layer Aircraft Structures," Topic #AF02-281, dated Jan. 14, 2002.
DOE Phase II Proposal, titled "Intelligent Probes for Enhanced Non-Destructive Determination of Degradation in Hot-Gas-Path Components," Topic #44c, dated Mar. 23, 2002.
Air Force Phase II Proposal, titled "Detection and Imaging of Damage, Including Hydrogen Embrittlement Effects in Landing Gear and Other High-Strength Steel Components," Topic #AF01-308, dated Apr. 9, 2002.
Strategic Environmental Research and Development Program Proposal, titled "High Resolution Inductive Sensor Arrays for UXO Detection, Identification and Clutter Suppression,", SON #UXSON-02-03, dated Apr. 17, 2002.
NASA Phase II Proposal, titled "Shaped Field Giant Magnetoresisitive Sensor Arrays for Materials Testing," Topic #01-II A1.05-8767, dated May 2, 2002.
Navy Phase I Proposal, titled "Observability Enhancement and Uncertainty Mitigation for Engine Rotating Component PHM," Topic #N02-188, dated Aug. 14, 2002.
NASA Phase I Proposal, titled "Non-Destructive Evaluation, Health Monitoring and Life Determination of Aerospace Vehicles/Systems," Topic #02-H5.03-8767, dated Aug. 21, 2002.
Final Report submitted to FAA, titled "Crack Detection Capability Comparison of JENTEK MWM-Array and GE Eddy-current Sensors on Titanium ENSIP Plates", dated Sep. 28, 2001, Contract #DTFA03-00-C-00026, option 2 CLIN006 and 006a.
Final Report submitted to FAA, titled "Aircraft Hidden Damage Detection and Assessment with Conformable Eddy Current Arrays," FAA Contract DTFA03-01-C-00024, dated Mar. 29, 2002.
Final Report submitted to NASA, titled "Shaped Field Giant Magnetoresisitive Sensor Arrays for Materials Testing," dated May 3, 2002.
Final Report submitted to Air Force, titled "Detection and Imaging of Damage, Including Hydrogen Embrittlement Effects in Landing Gear and Other High-Strength Steel Components," dated Jul. 3, 2002.
Final Report submitted to Navy, titled "Wireless Communications with Electromagnetic Sensor Networks for Nondestructive Evaluation," dated Jul. 15, 2002.
Final Report titled "Portable Accumulated Fatigue Damage Inspection System Using Permanently Mounted and Wide-Area Imaging MWM-Arrays," dated Aug. 23, 2002.
Technical paper titled "MWM Eddy-Current Arrays for Crack Initiation and Growth Monitoring," submitted to International Journal of Fatigue, from the International Conference on Fatigue Damage of Structural Materials IV, Hyannis, MA, 2002.
Technical paper titled "Conformable Eddy-Current Sensors and Arrays for Fleetwide Gas Turbine Component Quality Assessment," published in ASME Journal of Engineering for Gas Turbines and Power, vol. 124, No. 4, pp. 904-909; Oct. 2002.
Technical paper titled "Residual and Applied Stress Estimation from Directional Magnetic Permeability Measurements with MWM Sensors," published in ASME Journal of Pressure Vessel Technology, vol. 124, pp. 375-381; Aug. 2002.
Technical paper titled "Fatigue and Stress Monitoring Using Scanning and Permanently Mounted MWM-Arrays," presented at 29th Annual Review of Progress in QNDE; Bellingham, Washington; Jul. 2002.
Technical paper titled "Absolute Electrical Property Imaging using High Resolution Inductive, Magnetoresistive and Capacitive Sensor Arrays for Materials Characterization," presented at 11th International Symposium on Nondestructive Characterization of Materials, Berlin, Germany; Jun. 2002.
Technical paper titled "Application of MWM® Eddy-Current Technology during Production of Coated Gas Turbine Components," presented at 11th International Symposium on Nondestructive Characterization of Materials, Berlin, Germany; Jun. 2002.
Technical paper titled "Friction Stir Weld Inspection through Conductivity Imaging using Shaped Field MWM®-Arrays," presented at ASM Trends in Welding Conference, Callaway Gardens, GA; Apr. 2002.
Technical paper and presentation slides, titled "MWM-Array Characterization and Imaging of Combustion Turbine Components," presented at EPRI International Conference on Advances in Life Assessment and Optimization of Fossil Power Plants, Orlando, FL; Mar. 2002.
Technical paper titled "Surface Mounted and Scanning Periodic Field Eddy-Current Sensors for Structural Health Monitoring", presented at the IEEE Aerospace Conference, Mar. 2002.

Presentation slides titled "Corrosion Detection and Prioritization Using Scanning and Permanently Mountable MWM Eddy-Current Arrays," U.S. Army Corrosion Summit, Mar. 2002.

Technical paper and presentation slides titled "Shaped-Field Eddy-current Sensors and Arrays", SPIE 7th Annual International Symposium: NDE for Health Monitoring and Diagnostics, Mar. 2002.

Technical paper titled "Corrosion Detection and Prioritization Using Scanning and Permanently Mounted MWM Eddy-Current Arrays", Tri-Service Corrosion Conference, Jan. 2002.

Technical presentation slides "Condition Assessment of Engine Component Materials Using MWM Eddy-Current Sensors," ASNT Fall Conference, Columbus, OH; Oct. 2001.

Technical paper titled "Flexible Eddy Current Sensors and Scanning Arrays for Inspection of Steel and Alloy Components," 7th EPRI Steam Turbine/Generator Workshop and Vendor Exposition, Baltimore, MD; Aug. 2001.

Technical paper titled "Applications for Conformable Eddy Current Sensors including High Resolution and Deep Penetration Sensor Arrays in Manufacturing and Power Generation," ASME 7th NDE Topical Conference, San Antonio, Texas; 2001.

Air Force Phase II Proposal, titled "Three Dimensional Magnetic Imaging of Damage in Multiple Layer Aircraft Structures," Topic #AF02-281, dated Feb. 20, 2003.

Technical paper titled "*MWM Eddy Current Sensor Array Imaging of Surface and Hidden Corrosion for Improved Fleet Readiness and Cost Avoidance*," presented at U.S. Army Corrosion Conference, Clearwater Beach; FL, Feb. 11-13, 2003.

Technical paper titled "*MWM Eddy Current Sensor Array Characterization of Aging Structures Including Hidden Damage Imaging*" presented to the Aerospace Committee, NACE Conference, San Diego; CA, Mar. 17-19, 2003.

Bowler, N., "Theory of Four-Point Direct-Current Potential Drop Measurements on a Metal Plate," Research in Nondestructive Evaluation, vol. 17, pp. 29-48, (2006).

Navy Phase I Proposal, titled "In-situ projected field and near surface sensors for direct condition monitoring of engine hot section components," Topic #N06-T011, dated Apr. 13, 2006.

\* cited by examiner

APPLIED AND RESIDUAL STRESS MEASUREMENTS USING MAGNETIC FIELD SENSORS

RELATED APPLICATIONS

This application claims the benefit of U.S. Provisional Application No. 60/351,666, filed Jan. 25, 2002. The entire teachings of the above application are incorporated herein by reference.

BACKGROUND OF THE INVENTION

The technical field of this invention is that of nondestructive materials characterization, particularly quantitative, model-based characterization of surface, near-surface, and bulk material condition for flat and curved parts or components using magnetic field based or eddy-current sensors.

Characterization of bulk material condition includes (1) measurement of changes in material state, i.e., degradation/damage caused by fatigue damage, creep damage, thermal exposure, or plastic deformation; (2) assessment of residual stresses and applied loads; and (3) assessment of processing-related conditions, for example from aggressive grinding, shot peening, roll burnishing, thermal-spray coating, welding or heat treatment. It also includes measurements characterizing material, such as alloy type, and material states, such as porosity and temperature. Characterization of surface and near-surface conditions includes measurements of surface roughness, displacement or changes in relative position, coating thickness, temperature and coating condition. Each of these includes detection of electromagnetic property changes associated with either microstructural and/or compositional changes, or electronic structure (e.g., Fermi surface) or magnetic structure (e.g., domain orientation) changes, or with single or multiple cracks.

A specific application of these techniques is the inspection of high-strength steel components with the goal of measuring applied and residual stresses and detecting early stage fatigue damage and hydrogen embrittlement. Highly stressed aircraft components, such as landing gear components, require the use of steels such as 4340M and 300M heat treated to very high strength levels. The integrity of these components is critical to the safe operation of aircraft and for maintaining readiness of military aircraft. However, unintentional loading of these components, such as a hard landing, can impart residual stresses that compromise the integrity of the component. Similarly, the mechanical properties of these ultra-high strength steels can be seriously degraded as a result of the ingress of hydrogen. Hydrogen ingress can occur during pickling or plating operations and also during cleaning with citric acid based maintenance solutions. The resulting hydrogen embrittlement is unpredictable and can cause catastrophic failure of the component.

The detrimental effects of hydrogen on material properties and component integrity have been observed in a wide range of metals, as described for example in Interrante and in Hydrogen in Metals. Management of high-strength steel components embrittled by hydrogen is made more difficult by the fact that failures are typically delayed, occurring some time after ingress of atomic hydrogen. The delay between exposure to hydrogen and failure of a high strength steel component depends on a number of factors. Among these are the levels of hydrogen concentration, tensile stress, temperature, stress gradients, and certain impurities in the steel, as well as the type, concentration, and size of certain crystal lattice defects and inclusions. Moreover, susceptibility to hydrogen embrittlement can vary significantly between different heats of steels and between different pours from a given heat, as described by Lawrence. Hydrogen concentration on the order of a few parts per million is sufficient to cause hydrogen embrittlement and delayed fracture. Once atomic hydrogen enters the steel, excess hydrogen atoms diffuse to inclusions, preexisting defects, and zones of high dislocation density. Some hydrogen atoms, as a result of stress-assisted diffusion, can cluster and form "platelets" leading to initiation of microcracks. When such platelets form in front of a crack tip, they facilitate crack extension. Critical regions where hydrogen cracks are more likely to initiate are notches or other stress raisers where local hydrogen concentration is higher due to enhanced diffusion into the triaxially stressed region in front of a stress raiser. Cracks at these critical locations initiate close to but beneath the surface.

A recent review of existing magnetic/electromagnetic, diffraction, ultrasonic and other methods for assessment of residual stresses in steel components by Bray highlighted strengths and weaknesses of the available methods. This review also indicated that practical and cost-effective methods for assessment of residual stresses as well as for monitoring of applied stresses over wide areas in steel components are not yet available. Typically, discrete strain gages are mounted directly onto the material under test (MUT). However this requires intimate fixed contact between the strain gage and the MUT and individual connections to each of the strain gages, both of which limit the potential usefulness for monitoring stress over large areas. Possible correlations between magnetic properties and stresses in ferromagnetic materials have been studied for over 100 years, as reviewed by Bozorth. Magnetostriction effect data suggests that, depending on the magnitude and sign of the magnetostriction coefficient, correlation between stress and magnetic permeability within certain ranges of the magnetic field should be present. However, attempts to use conventional inductive, i.e., eddy-current sensors for assessment of residual stresses as well as for a number of other applications have shown serious limitations, particularly for complex geometry components.

Conventional eddy-current sensing involves the excitation of a conducting winding, the primary, with an electric current source of prescribed frequency. This produces a time-varying magnetic field at the same frequency, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

In many structures, fasteners such as bolts and rivets are used to hold various structural elements together. These fasteners also help to transfer the mechanical load on the structure between the various elements. The number, type, and size of fasteners used in a given structure are generally designed so that the loads on the fasteners are not excessive. This is accomplished using model stress calculations for expected applied loads and the geometries and mechanical properties of the various elements. However, unanticipated loads on the structure or local changes in the structure due to corrosion and/or fatigue can lead to excessive cyclic and sustained stresses, and fatigue failures of the fasteners and structural elements, which can compromise the integrity of the structure.

As an example, consider the accumulation of damage at multiple sites on aging aircraft. The cyclic loading of these aircraft over extended periods can lead to the formation of cracks at multiple locations, such as between fasteners in a lap joint. Individually, the growth of one of these cracks to the next fastener may not compromise the structural integrity, but it can alter the load distribution among the fasteners. This load redistribution around the nearby fasteners can accelerate crack propagation, if the cracks are already present, or cause initiation and propagation of other cracks. In either case, the capability to monitor the stress distribution in the fasteners can provide vital information about the load on the fastener and the structure.

SUMMARY OF THE INVENTION

Aspects of the methods described herein involve novel sensors and sensor arrays for the measurement of the near surface properties of conducting and/or magnetic materials. These sensors and arrays use novel geometries for the primary winding and sensing elements that promote accurate modeling of the response and provide enhanced capabilities for the creation of images of the properties of a test material.

In one embodiment, loads on a fastener are determined by placing a hollow fastener in a structural article and measuring the electrical properties of the fastener material from inside this fastener. Preferably the fastener material is a steel and the loads applied to the fastener are representative of the loads on the structure when in service. The fastener material may have a material property that is sensitive to the applied stress. An eddy-current sensor may be used and the stress-sensitive material property is an electrical property, such as a magnetic permeability or electrical conductivity. The eddy-current sensor may also have an array of sensing elements to monitor the stress or load distribution. The sensor array can be mounted to the inner surface of the fastener for continuous monitoring or periodically scanned across the inner surface to create images of the permeability distribution and, hence, the stress distribution.

These measurement methods can also be extended to monitoring the stress on a structural article as well by affixing a stress-sensitive material to the article, measuring the properties of this indicator material, and correlating these properties to the stress. The indicator material can be used to enhance the measurable signal due to stresses on materials whose electrical properties do not vary significantly with stress, such as aluminum. The indicator material can be mounted on the same side as the sensor which is used to inspect the surface. Alternatively, the indicator material can be placed on the opposite side of the test material, away from the sensor, so that the sensor must perform a remote measurement of the indicator material properties. In one embodiment of the invention, the electrical property variations with stress are measured with an eddy-current sensor. Preferably, the response is measured with an eddy-current sensor array. This array can be mounted against or scanned over the surface. In one embodiment of the invention, the stress-sensitive material is a magnetizable steel and the electrical property is the magnetic permeability. In another embodiment, it may be a nonmagnetizable metal and the electrical property is the electrical conductivity. Measurements of the indicator material properties do not require contact with the article or the indicator. To see through thick materials and for low frequency measurements, a giant magnetoresistive sensor element is used.

Another aspect of the invention includes methods for correlating electrical property measurements with a state of a material, such as the residual stress distribution, carbide content, or presence of grinding burn damage. Often these measurements are performed on materials having a complex geometry so the sensor for performing these measurements is preferably flexible and conformable. For inspecting wide areas, one embodiment of the invention may have a plurality of sensing elements, preferably aligned in a row or column, so that scanning of the array over the material surface can readily create an image of the material properties. Because the geometry for eddy-current sensors and sensor arrays are directional, with a preferential measurement of magnetic permeability or electrical conductivity depending upon the sensor orientation, the sensing elements may measure in two orthogonal orientations. Preferably, measurements are also performed at multiple frequencies to better characterize the material properties. In a preferred embodiment of the invention, the electrical property of the material being measured is the magnetic permeability.

In another aspect of the invention, a method is disclosed for monitoring the load on a magnetizable fastener with a sensor coil. Variations in the magnetic permeability of the fastener due to applied loads are detected with a coil mounted beneath the fastener head. The fastener material may be a non-austenitic steel. Alternatively, a second coil can be used in conjunction with the first coil to form a magnetic circuit to improve sensitivity to stress near the center of the fastener.

Images of the effective material properties taken with multiple sensor orientations may be used to distinguish isotropic (non-directional) properties from anisotropic (directional) properties. The sensor can be flexible. The sensor may be an eddy current sensor or an eddy current sensor array. The anisotropic property may be the residual stress. In another embodiment of the invention, the isotropic property is a grinding burn.

The sensor allows determination of maximum and minimum property magnitude orientations, i.e., directions. Preferably, the sensor response is measured in direction of maximum value of the effective property. In another embodiment of the invention, the sensor response may be measured in direction of the minimum in the effective property. Preferably, measurements are also performed at multiple frequencies to better characterize variations of the material properties with depth. The effective property of the material being measured may be the magnetic permeability, electrical conductivity, lift-off, or others.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The use of conformable eddy-current sensors and sensor arrays is described herein for the nondestructive characterization of materials, particularly as it applies to the characterization of applied and residual stresses. This sensing approach can be used to monitor the material characteristics at a given location with single or multiple sensing element sensors and sensor arrays using hand-held probes or mounted into automated scanners. In addition, the sensors can be mounted into a structure in proximity to a material under test for monitoring the property changes while the material is being stressed and fatigued. The sensors can also be used to detect process related changes in the material properties, such as grinding burns in steels either as a part of in-process monitoring or at any time after processing, i.e., during quality control inspections or in service.

A conformable eddy-current sensor suitable for these measurements, the Meandering Winding Magnetometer (MWM®), is described in U.S. Pat. Nos. 5,015,951, 5,453,689, and 5,793,206. The MWM is a "planar," conformable eddy-current sensor that is designed to support quantitative and autonomous data interpretation methods. These methods, called grid measurement methods, permit crack detection on curved surfaces without the use of crack standards, and provide quantitative images of absolute electrical properties (conductivity and permeability) and coating thickness without requiring field reference standards (i.e., calibration is performed in "air," away from conducting surfaces). MWM sensors and MWM-Arrays can be used for a number of applications, including fatigue monitoring and inspection of structural components for detection of flaws, degradation and microstructural variations, as well as for characterization of coatings and process-induced surface layers. Characteristics of these sensors and sensor arrays include directional multi-frequency magnetic permeability or electrical conductivity measurements over a wide range of frequencies, e.g., from 250 Hz to 40 MHz with the same MWM sensor or MWM-Array, high-resolution imaging of measured permeability or conductivity, rapid permeability or conductivity measurements with or without a contact with the surface, and a measurement capability on complex surfaces with a hand-held probe or with an automated scanner. This allows the assessment of applied and residual stresses as well as permeability variations in a component introduced from processes such as grinding operations.

Figure 1:
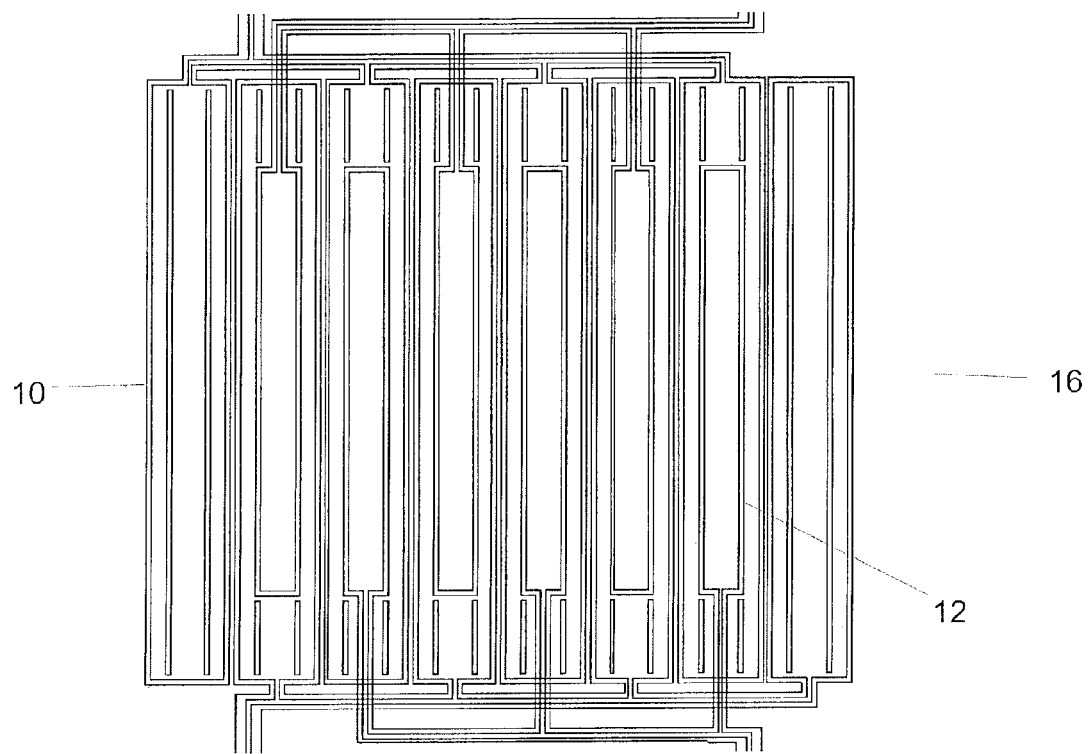
FIG. 1 is a schematic drawing of a spatially periodic field eddy-current sensor.

FIG. 1 illustrates the basic geometry of an MWM sensor 16, a detailed description of which is given in U.S. Pat. Nos. 5,453,689, 5,793,206, and 6,188,218 and U.S. patent application Serial Nos. 09/666,879 and 09/666,524, both filed on Sep. 20, 2000, the entire teachings of which are incorporated herein by reference. The sensor includes a primary winding 10 having extended portions for creating the magnetic field and secondary windings 12 within the primary winding for sensing the response. The primary winding 10 is fabricated in a spatially periodic pattern with the dimension of the spatial periodicity termed the spatial wavelength $\lambda$. A current is applied to the primary winding to create a magnetic field and the response of the MUT to the magnetic field is determined through the voltage measured at the terminals of the secondary windings. This geometry creates a magnetic field distribution similar to that of a single meandering winding. A single element sensor has all of the sensing elements connected together. The magnetic vector potential produced by the current in the primary can be accurately modeled as a Fourier series summation of spatial sinusoids, with the dominant mode having the spatial wavelength $\lambda$. For an MWM-Array, the responses from individual or combinations of the secondary windings can be used to provide a plurality of sense signals for a single primary winding construct as described in U.S. Pat. No. 5,793,206 and Pat. No. Re. 36,986.

Figure 2:
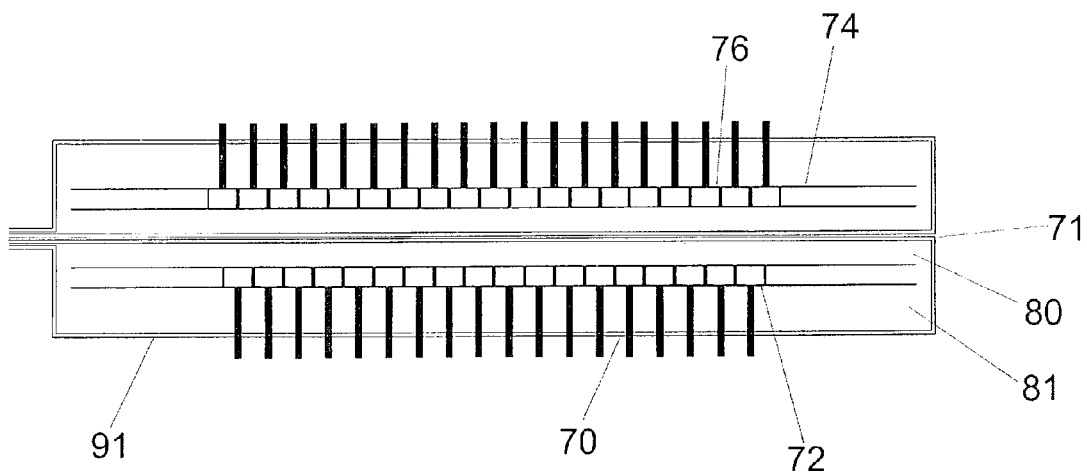
FIG. 2 is an expanded view of drive and sense elements for an eddy-current array having offset rows of sensing elements.
Figure 3:
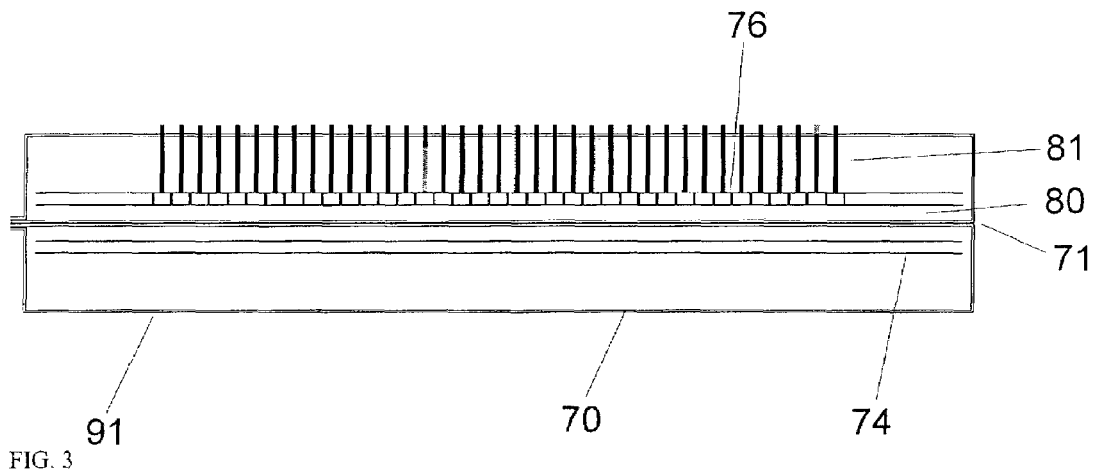
FIG. 3 is an expanded view of drive and sense elements for an eddy-current array having a single row of sensing elements.
Figure 4:
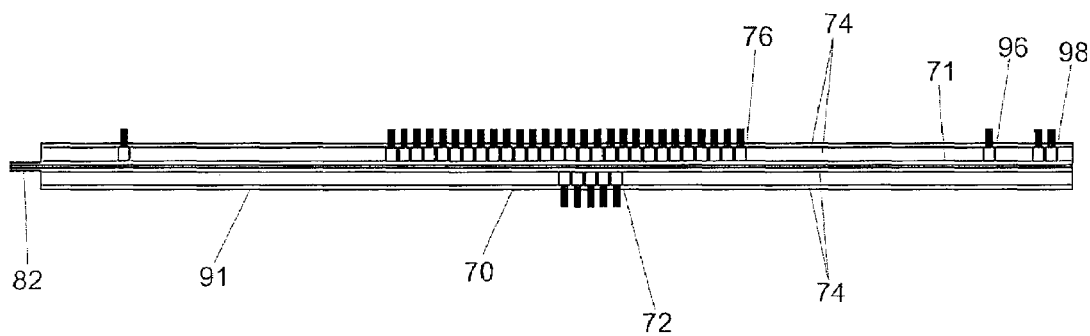
FIG. 4 is an expanded view of an eddy-current array where the locations of the sensing elements along the array are staggered.

In another embodiment, eddy-current sensor arrays comprised of at least one meandering drive winding and multiple sensing elements are used to inspect the test material. Example sensor arrays are shown in FIG. 2 through FIG. 4 and are described in detail in U.S. patent application Ser. No. 10/102,620, filed Mar. 19, 2002, the entire teachings of which are incorporated herein by reference. This array includes a primary winding 70 having extended portions for creating the magnetic field and a plurality of secondary elements 76 within the primary winding for sensing the response to the MUT. The secondary elements are pulled back from the connecting portions of the primary winding to minimize end effect coupling of the magnetic field. Dummy elements 74 can be placed between the meanders of the primary to maintain the symmetry of the magnetic field, as described in U.S. Pat. No. 6,188,218. When the sensor is scanned across a part, or when a crack propagates across the sensor, perpendicular to the extended portions of the primary winding, secondary elements 72 in a primary winding loop adjacent to the first array of sense elements 76 provide a complementary measurement of the part properties. These arrays of secondary elements 72 can be aligned with the first array of elements 76 so that images of the material properties will be duplicated by the second array. Alternatively, to provide complete coverage when the sensor is scanned across a part the sensing elements, it can be offset along the length of the primary loop, or when a crack propagates across the sensor, perpendicular to the extended portions of the primary winding, as illustrated in FIG. 2.

The dimensions for the sensor array geometry and the placement of the sensing elements can be adjusted to improve sensitivity for a specific inspection. For example, the effective spatial wavelength, or the distance between the central conductors 71 and the current return conductor 91, can be altered to adjust the sensitivity of a measurement for a particular inspection. For the sensor array of FIG. 2, the distance 80 between the secondary elements 72 and the central conductors 71 is smaller than the distance 81 between the sensing elements 72 and the return conductor 91. An optimum response can be determined with models, empirically, or with some combination of the above. An example of a modified sensor design is shown FIG. 3. In this sensor array, all of the sensing elements 76 are on one side of the central drive windings 71. The size of the sensing elements and the gap distance 80 to the central drive windings 71 are the same as in the sensor array of FIG. 2. However, the distance 81 to the return of the drive winding has been increased, as has the drive winding width to accommodate the additional elements in the single row of elements. Another example of a modified design is shown in FIG. 4. Here, most of the sensing elements 76 are located in a single row to provide the basic image of the material properties. A small number of sensing elements 72 are offset from this row to create a higher image resolution in a specific location. Other sensing elements are distant from the main grouping of sensing elements at the center of the drive windings to measure relatively distant material properties, such as the base material properties for plates at a lap joint or a weld.

In one embodiment of the invention, the number of conductors used in the primary winding can be reduced further so that a single rectangular drive is used. A single loop having extended portions can be used for the primary winding. A row of sensing elements is placed on the outside of one of the extended portions. This is similar to designs described in U.S. Pat. No. 5,453,689, where the effective wavelength of the dominant spatial field mode is related to the spacing between the drive winding and sensing elements. This spacing can be varied to change the depth of sensitivity to properties and defects. Advantages of such a design include a narrow drive and sense structure that allows measurements close to material edges and non-crossing conductor pathways so that a single layer design can be used with all of the conductors in the sensing region in the same plane. The width of the conductor farthest from the sensing elements can be made wider in order to reduce an ohmic heating from large currents being driven through the drive winding.

The MWM sensor and sensor array structure can be produced using micro-fabrication fabrication techniques typically employed in integrated circuit and flexible circuit manufacture. This results in highly reliable and highly repeatable (i.e., essentially identical) sensors, which has inherent advantages over the coils used in conventional eddy-current sensors. As indicated by Auld and Moulder, for conventional eddy-current sensors "nominally identical probes have been found to give signals that differ by as much as 35%, even though the probe inductances were identical to better than 2%"[Auld, 1999]. This lack of reproducibility with conventional coils introduces severe requirements for calibration of the sensors (e.g., matched sensor/calibration block sets). In contrast, duplicate MWM sensor tips have nearly identical magnetic field distributions around the windings as standard micro-fabrication (etching) techniques have both high spatial reproducibility and resolution. As the sensor was also designed to produce a spatially periodic magnetic field in the MUT, the sensor response can be accurately modeled which dramatically reduces calibration requirements. For example, calibration in air can be used to measure an absolute electrical conductivity without calibration standards, which makes the sensor geometry well-suited to surface mounted or embedded applications where calibration requirements will be necessarily relaxed.

For applications at temperatures up to 120° C. (250° F.), the windings are typically mounted on a thin and flexible substrate, producing a conformable sensor. A higher temperature version has shown a good performance up to about 270° C. (520° F.). The sensors, which are produced by microfabrication techniques, are essentially identical resulting in highly reliable and highly repeatable performance with inherent advantages over the coils used in conventional eddy-current sensors providing both high spatial reproducibility and resolution. For conformable sensors, the insulating layers can be a flexible material such as Kapton™, a polyimide available from E. I. DuPont de Nemours Company, while for high temperature applications the insulating layers can be a ceramic such as alumina.

For measuring the response of the individual sensing elements in an array, multiplexing between the elements can be performed. However, this can significantly reduce the data acquisition rate, so a more preferable approach is to use an impedance measurement architecture that effectively allows the acquisition of data from all of the sense elements in parallel. Furthermore, ability to measure the MUT properties at multiple frequencies extends the capability of the inspection to better characterize the material and/or geometric properties under investigation. This type of instrument is described in detail in U.S. patent application Ser. No. 10/155,887, filed May 23, 2002, the entire teachings of which are incorporated herein by reference. The use of multiple sensing elements with one meandering drive and parallel architecture measurement instrumentation then permits high image resolution in real-time and sensitivity with relatively deep penetration of fields into MUT.

An efficient method for converting the response of the MWM sensor into material or geometric properties is to use grid measurement methods. These methods map the magnitude and phase of the sensor impedance into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares squares error between the measurements and the predicted responses from the sensor.

An advantage of the measurement grid method is that it allows for real-time measurements of the absolute electrical properties of the material and geometric parameters of interest. The database of the sensor responses can be generated prior to the data acquisition on the part itself, so that only table lookup operation, which is relatively fast, needs to be performed. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations and instrument preparation.

Figure 5:
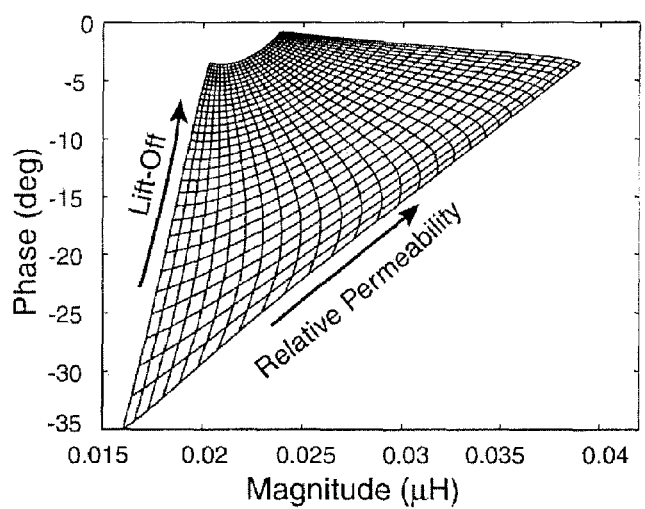
FIG. 5 illustrates a representative measurement grid relating the magnitude and phase of the sensor terminal impedance to the lift-off and magnetic permeability.
Figure 6:
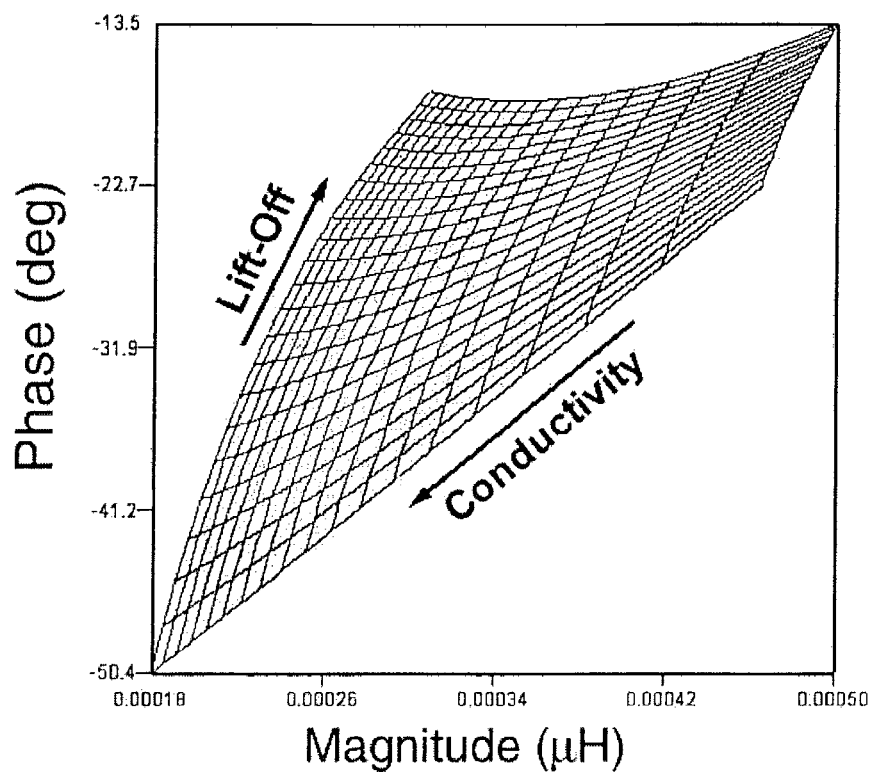
FIG. 6 illustrates a representative measurement grid relating the magnitude and phase of the sensor terminal impedance to the lift-off and electrical conductivity.

For ferromagnetic materials, such as most steels, a measurement grid provides conversion of raw data to magnetic permeability and lift-off. A representative measurement grid for ferromagnetic materials (e.g., carbon and alloy steels) is illustrated in FIG. 5. A representative measurement grid for a low-conductivity nonmagnetic alloy (e.g., titanium alloys, some superalloys, and austenitic stainless steels) is illustrated in FIG. 6.

Robust directional magnetic permeability measurements by MWM sensors and MWM-Arrays with grid methods allow estimation of stresses by taking advantage of the magnetostriction effect. For steels, at magnetic fields typical of those used for MWM, the magnetostriction coefficient generally is positive, so that the magnetic permeability increases with stress. Thus, once a correlation between stress and MWM measured magnetic permeability is established, stresses can be estimated as long as baseline information is available.

The capability to perform directional permeability measurements allows characterization of both uniaxial and biaxial stresses. In the latter case, the MWM permeability measurements at various sensor orientations reveal the directions of the principal stresses. Furthermore, permeability data from multifrequency MWM measurements can be used for reconstruction of stress distribution with depth. For typical excitation frequencies in the several kHz to several MHz range, the depth of penetration of the magnetic field is limited to a fairly thin layer near the surface, e.g., the first 0.5mm (0.02 in.). However, lowering the excitation frequency, for example down to several Hz, and using alternative sensing elements such as magnetoresistive or giant magnetoresistive sensors, as described for example in U.S. patent application Ser. No. 10/045,650, filed Nov. 8, 2001, the entire teachings of which are incorporated herein by reference, permits measurements to a significantly greater depth. Also, MWM-Arrays allow imaging of stress distributions over wide areas.

Figure 7:
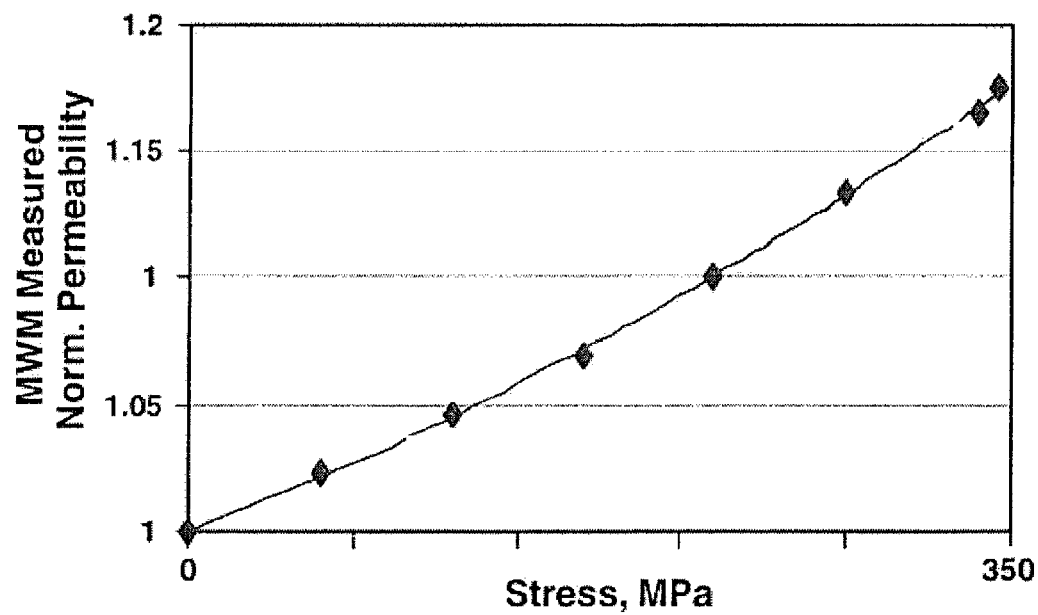
FIG. 7 is a plot of the correlation between MWM measured permeability and maximum stress in loading sequences used in the tests.
Figure 33:
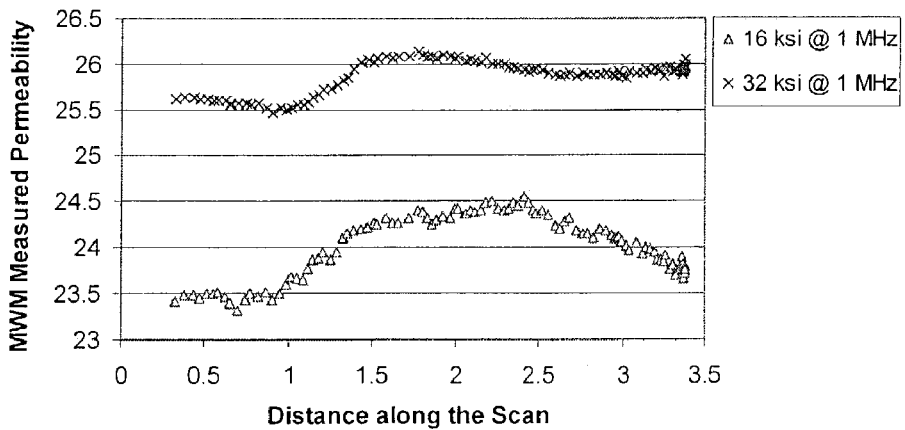
FIG. 33 illustrates a plot of MWM measured permeability scans along the axis of a 4340 steel tensile specimen containing semicircular notches, at two levels of applied stress. The distance along the scan is in inches.
Figure 34:
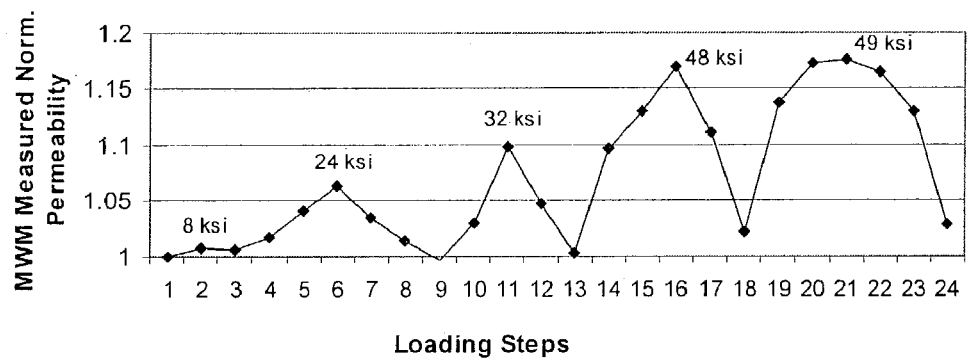
FIG. 34 illustrates a plot of MWM measured permeability for a five load-unload sequence.
Figure 35:
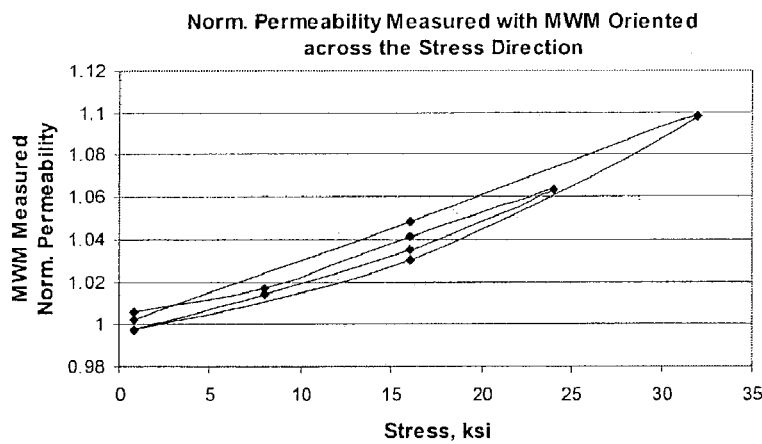
FIG. 35 illustrates a plot of MWM measured permeability for the loads achieved on the increasing and decreasing portions of a load-unload sequence.

An example of a permeability measurement scan with a single element sensor over a 4340 steel dogbone specimen with semicircular notches installed in a 90 kN (20,000-lb) Instron frame is shown in FIG. 33. In this case, the highest stress is expected at the 1.75-in. position with the highest estimated nominal stress in the narrow section between the semicircular notches at 16 and 32 ksi, respectively. Magnetic penneability measurements were performed prior to each loading sequence, i.e., at no load and at various levels of tensile load in an incremental load-unload sequence. The results shown in FIG. 33 were obtained at a frequency of 1 MHz. Multiple frequency MWM measurements can provide information on stress distribution with depth, as discussed later in reference to FIG. 8 through FIG. 11. FIG. 34 shows permeability changes in five load-unload sequences to a maximum estimated nominal stress of 8, 24, 32, 48, and 49 ksi. The pattern of the magnetic permeability changes actually reflects the loading pattern. The permeability-load curves shown in FIG. 34 illustrates a hysteresis between penneability measured at loads achieved on the increasing and decreasing portions of a loading sequence. This hysteresis is caused by a "delay" in rotation of magnetic domains on unloading. FIG. 7 shows the corresponding correlation between MWM measured permeability and the maximum stress reached in each loading sequence. At each loading step, a 90-mm by 25-mm rectangular area was scanned on both sides of the specimen with the MWM sensor shown in FIG. 1 mounted on a standard MWM probe. As shown in FIG. 7, the magnetic permeability, as measured by the MWM, is strongly correlated with applied tensile stress. These and other stress measurement results are described in more detail in the Air Force proposal "Detection and Imaging of Damage, Including Hydrogen Embrittlement Effects in Landing Gear and Other High-Strength Steel Components."

Figure 8:
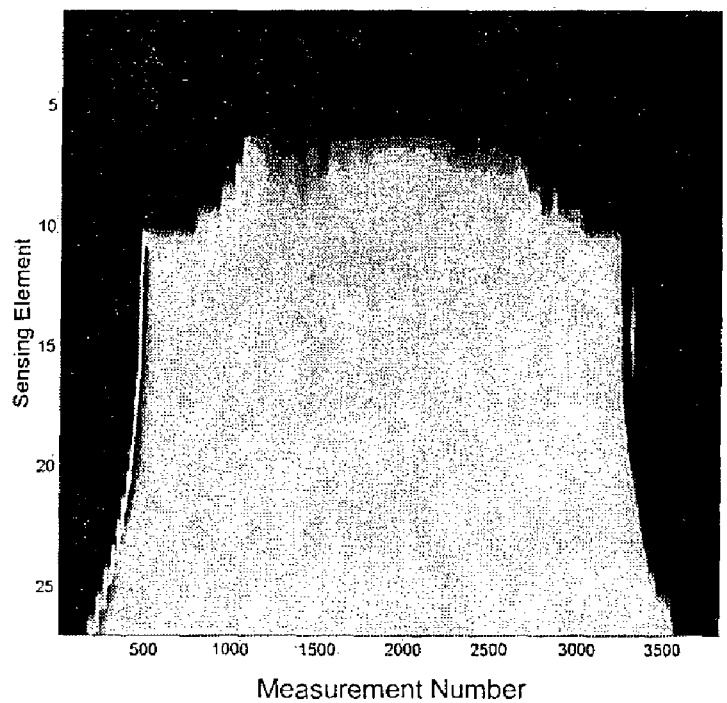
FIG. 8 illustrates a normalized permeability image obtained from an MWM-Array scanned over a double-notched 4340 low-alloy steel tensile specimen after failure in a tension test, with an excitation frequency of 1 MHz and the extended portions of the primary winding oriented parallel to the loading axis.
Figure 9:
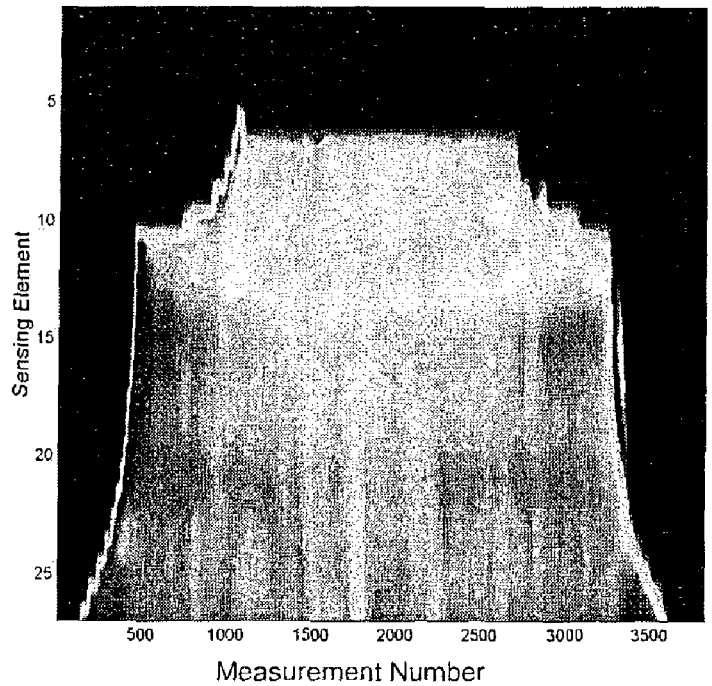
FIG. 9 illustrates a normalized permeability image obtained from an MWM-Array scanned over a double-notched 4340 low-alloy steel tensile specimen after failure in a tension test, with an excitation frequency of 158 kHz and the extended portions of the primary winding oriented parallel to the loading axis.
Figure 10:
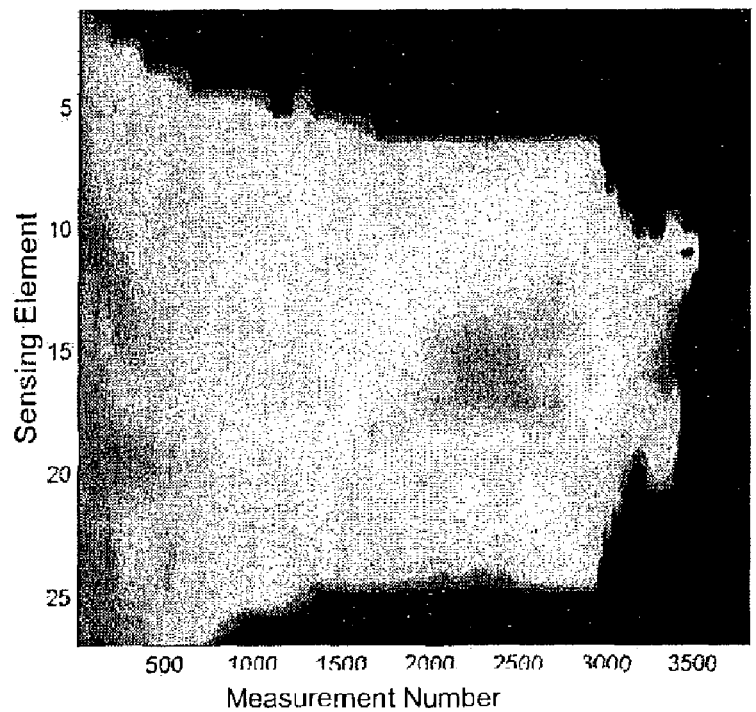
FIG. 10 illustrates a normalized permeability image obtained from an MWM-Array scanned over a double-notched 4340 low-alloy steel tensile specimen after failure in a tension test, with an excitation frequency of 1 MHz and the extended portions of the primary winding oriented perpendicular to the loading axis.
Figure 11:
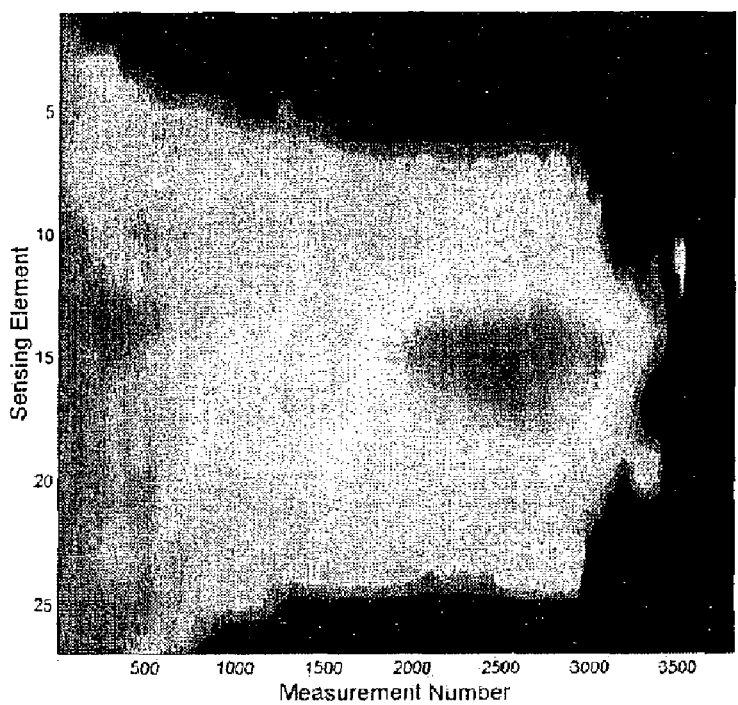
FIG. 11 illustrates a normalized permeability image obtained from an MWM-Array scanned over a double-notched 4340 low-alloy steel tensile specimen after failure in a tension test, with an excitation frequency of 158 kHz and the extended portions of the primary winding oriented perpendicular to the loading axis.
Figure 12:
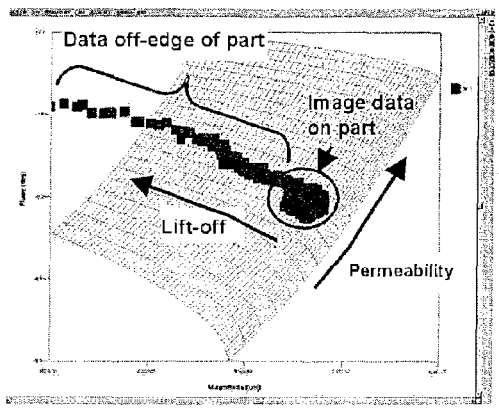
FIG. 12 illustrates a permeability/lift-off measurement grid and data from a single element of an MWM-Array.

MWM-Arrays also provide a capability to perform bidirectional magnetic permeability measurements in a scanning mode. FIG. 8 through FIG. 11 provide images of the magnetic permeability for a broken tensile specimen of 4340 low alloy steel. The MWM-Array was scanned across and along the gage section of a specimen broken in a tensile test and the permeability was measured at two frequencies, 158 kHz for FIG. 9 and FIG. 11 and 1 MHz for FIG. 8 and FIG. 10. In FIG. 8 and FIG. 9 the extended portions of the primary winding were oriented parallel to the loading axis. In FIG. 10 and FIG. 11 the extended portions of the primary winding were oriented perpendicular to the loading axis. This illustrates the potential to map residual stress variations produced in parts fabricated from carbon and low alloy steels, for example by a hard landing in the latter case. Notice that the permeability images at low and high frequencies reveal stress changes with distance from the surface. A high residual stress region near the fracture is indicated in the images of FIG. 10 and FIG. 11. To create these images, a permeability/lift-off measurement grid was used, as shown in FIG. 12, assuming a known conductivity and an infinite half-space (i.e., the steel layer is assumed to be infinitely thick). Since the lift-off or distance between the sensing windings and the test material is being measured through the measurement grids, the residual stress measurement can be performed in a non-contact mode, which ensures that the sensor and probe assembly do not influence the stress distribution on the component.

Figure 13:
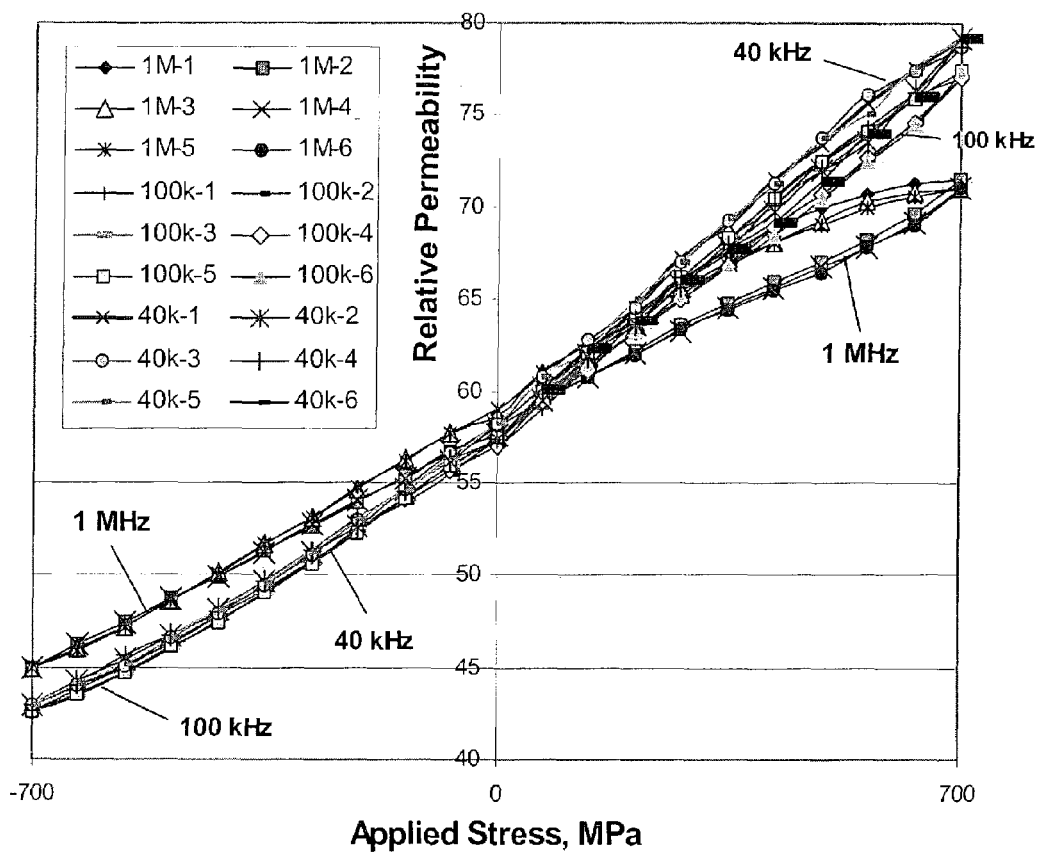
FIG. 13 illustrates the MWM measured magnetic permeability versus bending stress in a high-strength steel specimen at stresses from −700 to 700 MPa. The specimen was shot peened.

MWM permeability measurements on 300M high-strength steel specimens under fully reversed bending loading provide further indication of the capability of MWM sensors to perform stress measurements. The tests were performed on flat shot-peened specimens installed in a bending fixture. The stress range used in the test was between −700 MPa in compression and 700 MPa in tension. The stresses were determined from strains measured with a BLH strain gage using BLH instrumentation. The strain gages were attached to the "back" side. MWM magnetic permeability measurements were performed with the longer segments of the MWM drive winding perpendicular to the bending stress direction. In this orientation, the MWM measures permeability in the specimen longitudinal direction. FIG. 13 shows how the permeability measured at frequencies of 40 kHz, 100 kHz, and 1 MHz changes with applied bending stress. The data illustrate the sensitivity and quality of the permeability measurements for stress measurements in high strength steels over a wide range of stresses. The results clearly show the sensitivity of the MWM measurements to stress changes and reasonably small hysteresis, particularly in the compressive stress range.

Figure 14:
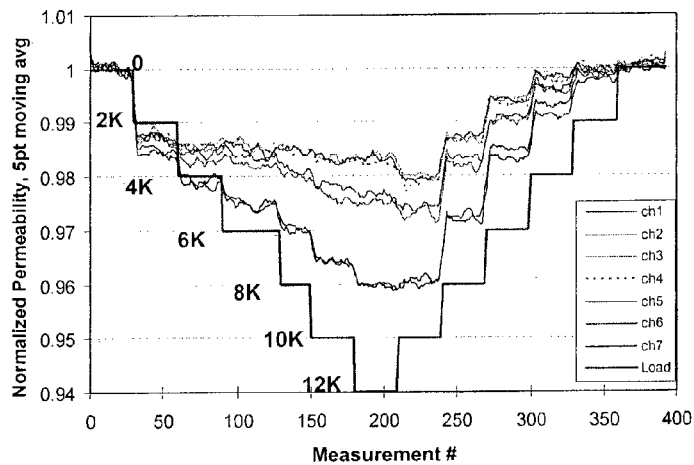
FIG. 14 illustrates MWM measured transverse permeability changes at incrementally increasing and decreasing tensile load (maximum load=53.4 kN (12,000 lbs); increment=8.9 kN (2,000 lbs)).
Figure 36:
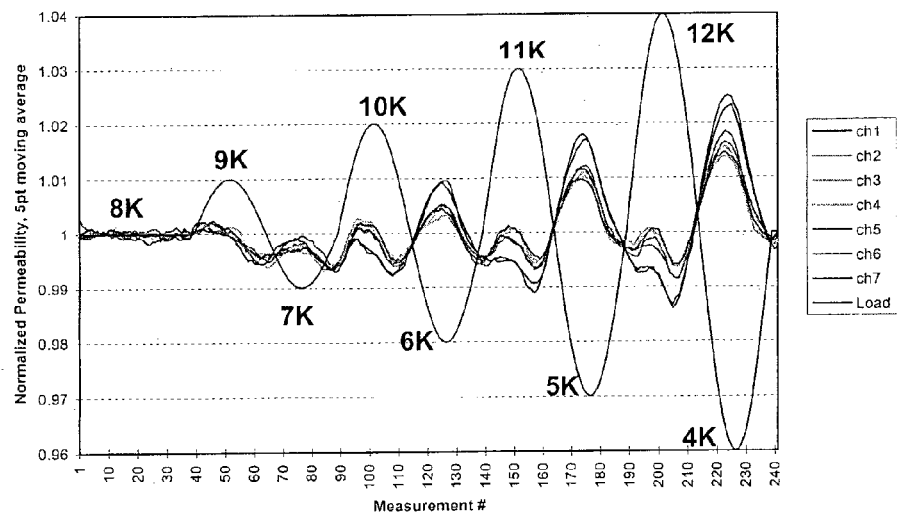
FIG. 36 illustrates a plot of MWM measured transverse permeability changes for a cyclically changing tensile load.

FIG. 14 shows the results of another set of tests illustrating the magnetic permeability changes due to the Poisson's effect or the transverse contraction under tensile axial load. A 7-channel MWM-Array was mounted on the specimen with the longer segments of the MWM-Array drive oriented along the specimen axis, i.e., parallel to tensile load orientation during tests, so that the magnetic permeability in the transverse direction is measured. In this test, the tensile load was first incrementally increased by 8.9 kN (2,000 lbs) to the maximum tensile load of 53.4 kN (12,000 lbs) and then incrementally decreased to 0. The estimated maximum axial stress in the center of the area was about 700 MPa (100 ksi). After each load increment, a constant load was maintained for a period of time. The loading pattern and MWM-Array measured transverse permeability in all seven channels is shown in FIG. 14. The observed change in MWM-Array measured transverse permeability appears to mimic changes in transverse strain. The lowest permeability changes occur near the center. The results emphasize the importance of permeability measurements and suggest that bidirectional permeability measurements are critical to stress measurements even under uniaxial loading. Similar results are obtained with the cyclic loading pattern of FIG. 36, which had a mean load of 8,000 lbs and load amplitude progressively increasing from 1,000 lbs (load range of 2,000 lbs) to 4,000 lbs (load range of 8,000 lbs).

The ability to detect and image stress distributions has implications for the detection and imaging of early stage fatigue damage as well. Fatigue tests of 4340 steel specimens revealed the capability to detect precrack damage early in the fatigue life. These specimens were designed with a cylindrical cavity in the gage section, where an MWM-Array could be mounted, and reinforcement ribs on the back side. This provides a nonuniform stress distribution with the maximum stress in the central portion of the cavity, as verified by a finite element analysis and described in more detail in "MWM Eddy-Current Arrays for Crack Initiation and Growth Monitoring," beneath the footprint of the MWM-Array. The shape and stress distribution within the cylindrical cavity can be varied to simulate the geometry of high strength steel components of interest.

Figure 37:
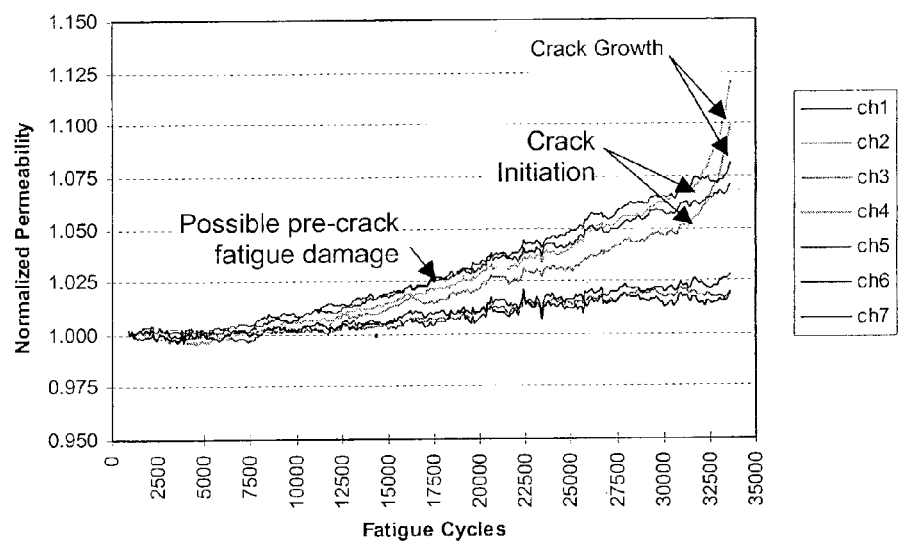
FIG. 37 illustrates a plot of normalized permeability against the number of fatigue cycles for a shot peened 4340 steel specimen.
Figure 38:
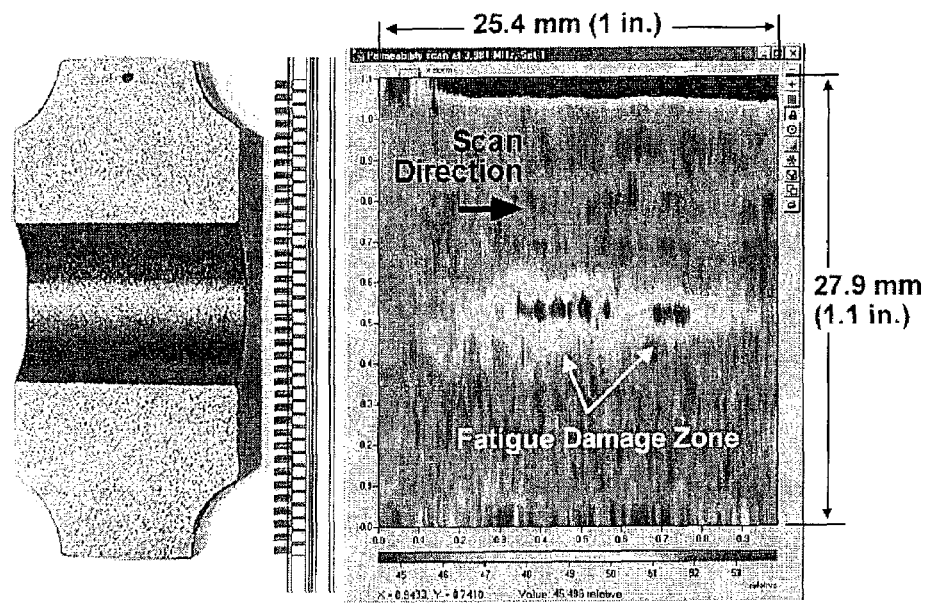
FIG. 38 illustrates an image of the MWM measured permeability of the fatigue damage zone at the end of the fatigue test.

FIG. 37 shows the permeability changes during a test using a 7-channel MWM-Array There is virtually no change in the measured permeability up to 7,000 cycles. The change in the slope of MWM measured permeability in the four centrally located channels at about 7,000 cycles is most likely associated with precrack fatigue damage. This fatigue damage stage extends, perhaps, up to 17,000 cycles followed by initiation and extension of multiple microcracks. Two of the channels show a significant permeability increase at 32,000 cycles indicating coalescence of closely spaced cracks and faster crack growth. SEM analysis on this specimen revealed a few small cracks, with the longest crack approximately 200 μm (0.008 in.) long. This crack was also confirmed by fluorescent liquid penetrant inspection (FPI). The FPI indication appeared as a tiny "speck" judged to be on the order of 0.25-mm (0.01-in.) long. The fatigue critical area of this specimen was also scanned with an imaging MWM-Array, with the drive oriented perpendicular to the axis of the coupon cavity. This orientation is perpendicular to anticipated predominant orientation of fatigue cracks, and is the same as in fatigue test monitoring of FIG. 37. FIG. 38 shows a permeability image and aligned intermittent regions of increased permeability having a combined length of about 20 mm (0.75-in.) Three of these regions appear to contain short indications characterized by the highest measured permeability. The other relatively high permeability regions are likely to indicate stress relaxation due to the cyclic loading and fatigue damage prior to formation of detectable cracks. These regions of enhanced permeability are also consistent with the higher stress region of the component from the finite element analysis.

Figure 15:
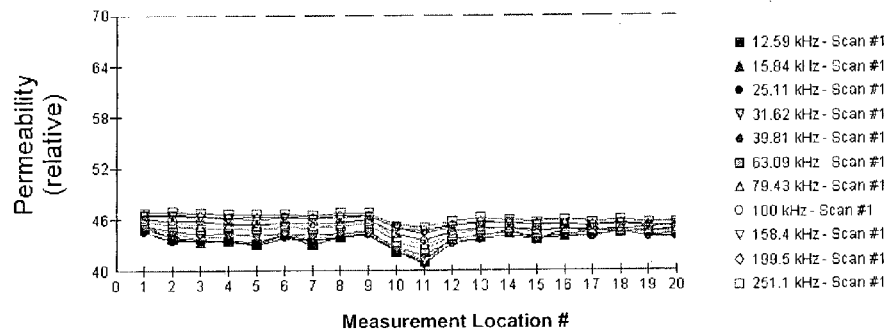
FIG. 15 illustrates a multifrequency MWM permeability scan over an area with gentle grinding in a high-strength steel component. The component was originally shot peened.
Figure 16:
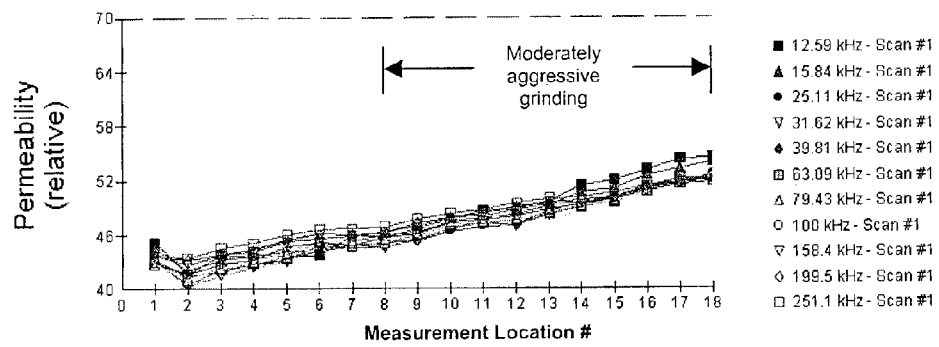
FIG. 16 illustrates a multifrequency MWM permeability scan over an area with moderately aggressive grinding in a high-strength steel component. The component was originally shot peened.
Figure 17:
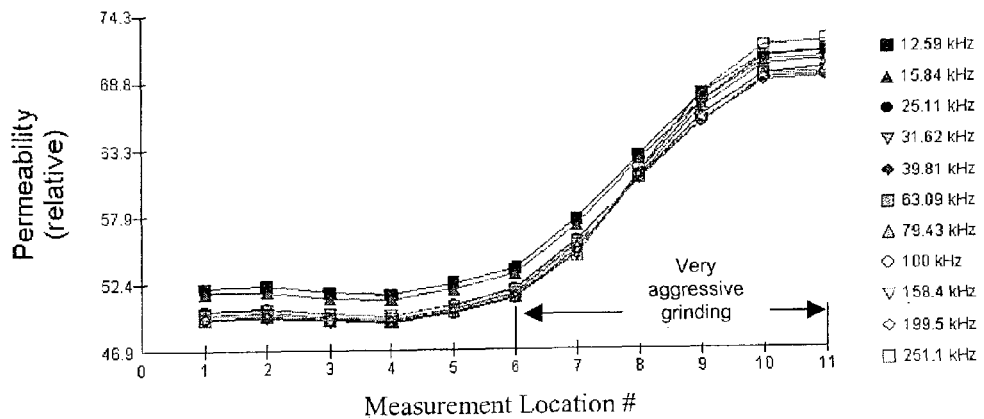
FIG. 17 illustrates a multifrequency MWM permeability scan over an area with very aggressive grinding in a high-strength steel component. The component was originally shot peened.
Figure 18:
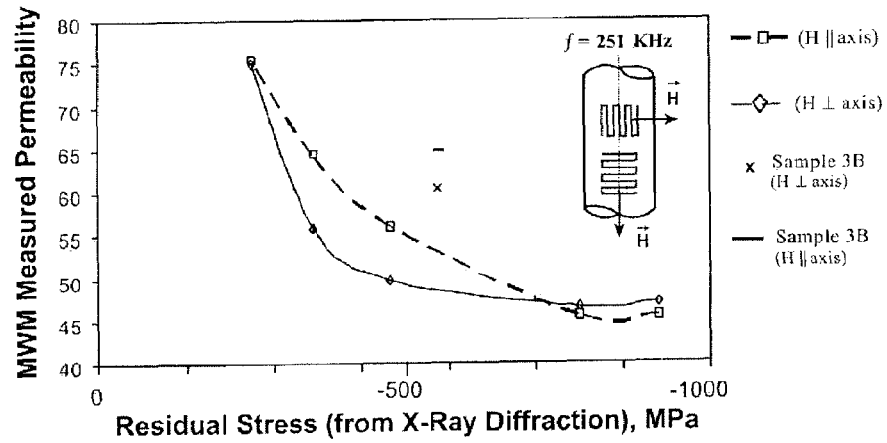
FIG. 18 illustrates a comparison between MWM measured permeability and compressive residual stress (from X-ray diffraction) in a high-strength steel component.

The capability of the MWM to assess grinding process quality and detect carbide content and other metallurgical and material features of interest has also been demonstrated. Hand grinding is commonly performed when repairing high-strength steel components. However, the grinding process itself can cause thermal damage or alter the stress distribution (through, for example, the reduction of compressive stresses originally introduced by shot peening) when not performed properly. FIG. 15 to FIG. 17 show results of MWM scanning of the shot peened components that were purposely prepared to replicate grinding representative of acceptable conditions as well as those that would be unacceptable for repairs of the components. FIG. 15 corresponds to a grind out obtained by gentle grinding. Here, the MWM measured magnetic permeability in the grind out area is virtually identical to the magnetic permeability of steel in the area that is outside the grind out. Thus, there is no evidence of any significant changes in magnetic permeability due to the gentle grinding, which suggests that the repair did not change compressive stresses induced by shot peening. FIG. 16 corresponds to a grind out obtained by "moderately aggressive" grinding and shows a slight increase in magnetic permeability in the grind out area. FIG. 17 corresponds to a grind out obtained by "very aggressive" grinding and shows a pronounced increase in magnetic permeability in the grind out area. The observed increase in permeability caused by grinding could correspond, at least partially, to relief of the compressive stresses induced by shot peening. FIG. 18 presents a plot of MWM permeability measured in the ground areas against the stress determined by X-ray diffraction measurements. This plot is qualitatively consistent with the plot in FIG. 13, i.e., lower absolute values of compressive stresses associated with increased intensity of grinding in FIG. 18 correspond to higher MWM measured permeability. Note that the penneability changes caused by aggressive grinding were quite likely affected by grinding burns as well. The combined effects of stress relaxation and microstructural changes complicate an assessment of residual stresses. However, such as separation is not always necessary when large local permeability changes can be used to judge a material condition to be unacceptable.

Figure 19:
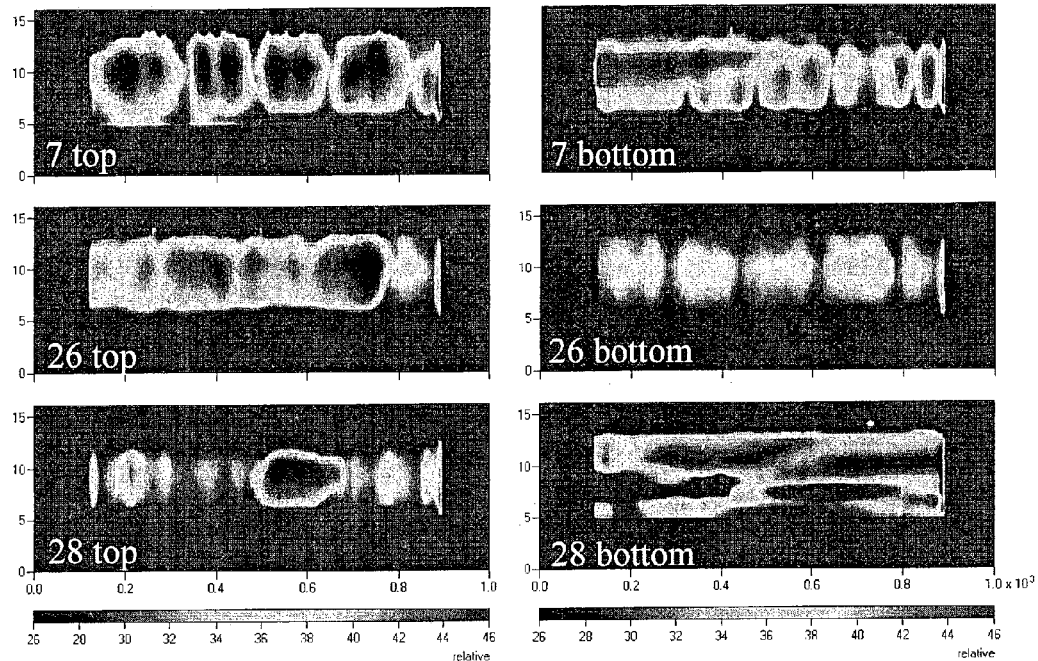
FIG. 19 illustrates a set of permeability images obtained from MWM-Array longitudinal scans over the top and bottom surfaces of three samples with grinding burns.
Figure 20:
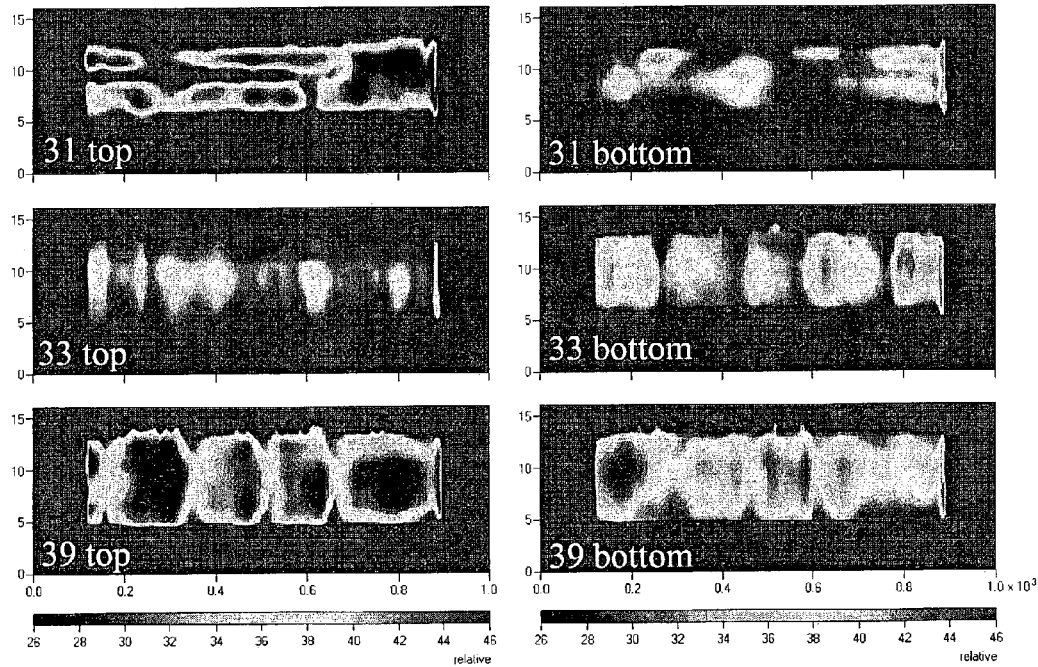
FIG. 20 illustrates another set of permeability images obtained from MWM-Array longitudinal scans over the top and bottom surfaces of three samples with grinding burns.

Images of the areas of samples exhibiting grinding burns have also been taken with MWM-Arrays. The sensor array used for these images had 16 active sensing elements, with each sensing element approximately 0.0625-in. by 0.040-in. in size. Measurements were taken at a frequency of 158 kHz with both manual and automated scanners. The samples were approximately 0.625-in. wide and 2.44-in. long. FIG. 19 and FIG. 20 shows sets of images taken on both sides of six samples (labeled 7, 26, 28, 31, 33, and 39) having grind burns with a longitudinal scan where the drive windings are perpendicular to the longest dimension of the sample. For these longitudinal scans, the samples were positioned approximately between channels 6 and 15, and the horizontal scale for each image is 1000 data points, which corresponds to a 3.15-in. scan length. The start and stop positions for each scan were off of the sample surface so that the response at the sample edges could also be observed.

Figure 21:
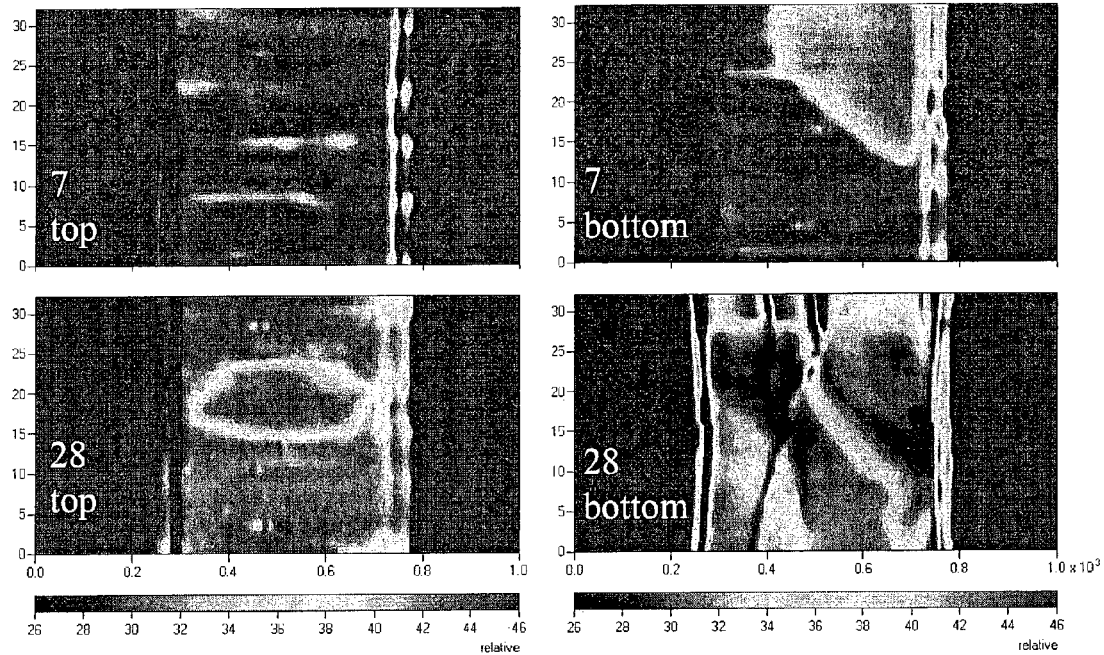
FIG. 21 illustrates a set of permeability images obtained from MWM-Array transverse scans over the top and bottom surfaces of two samples with grinding burns.

The images show a combination of the grinding burns and residual stress patterns across the sample surface. Distinct grinding burns were visually observed in the center of the top of sample 28 and in a triangular shape on the upper left side of the bottom of sample 7. These grinding burns were also observed in the permeability images. FIG. 21 shows a set of scan images for samples 7 and 28 with transverse scans where the drive windings are parallel to the longest dimension of the samples. In this case, two scans of 16 channels each, which span approximately 1.1 in., were concatenated together so that the resultant images covered 32 channels or approximately 2.2 in. These scans still show the distinct areas of grinding burns, but the permeability variations due to the residual stress distribution are different than with the longitudinal scans, as expected. Thus, the combination of images taken in two preferably orthogonal orientations, allows a non-directional property variation, such as associated with microstructure in the grinding burn areas, to be separated from a directional property variation, such as the residual stresses. In a preferred embodiment, one orientation will be in the direction of the maximum for a directional property while the other orientation would be in the direction of a minimum. This is one form of a spatial filter that can be performed efficiently with a high-resolution imaging array. Another spatial filtering approach that compares measured responses to shape responses for known flaws, including cracks, can also be performed, as described in more detail in, for example, U.S. patent application Ser. No. 10/155,887.

Figure 22:
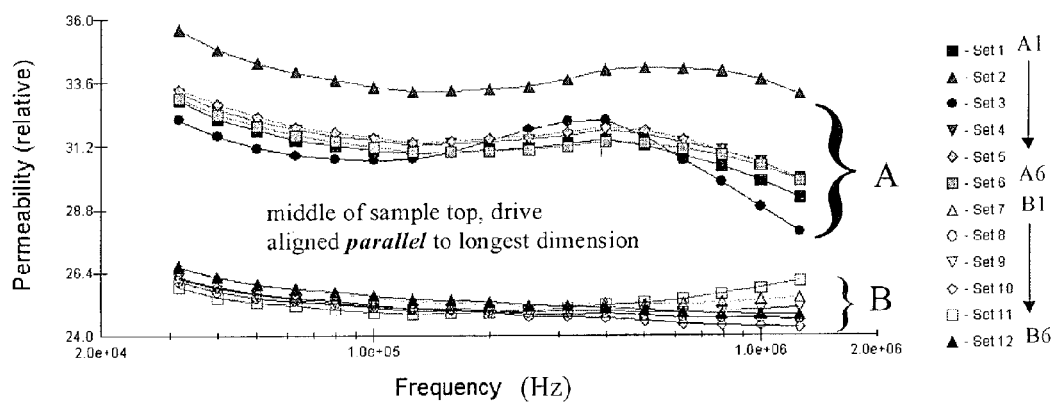
FIG. 22 illustrates a multiple frequency MWM permeability data over the middle of the top of sample sets A and B with the drive windings aligned parallel to the longest dimension of the sample.
Figure 23:
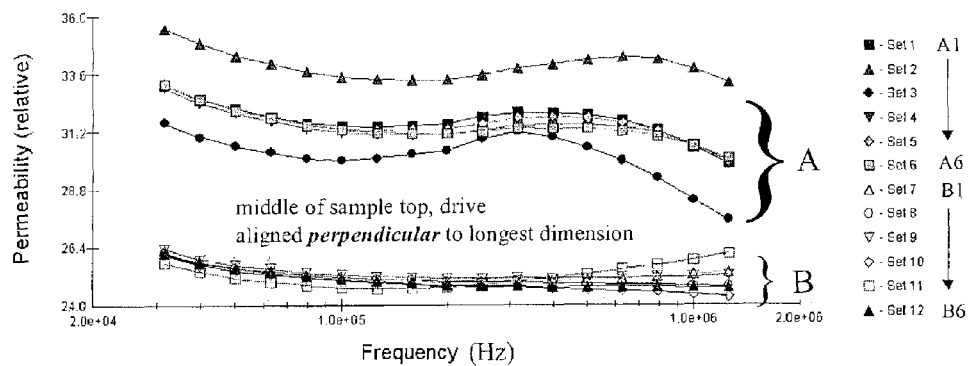
FIG. 23 illustrates a multiple frequency MWM permeability data over the middle of the top of sample sets A and B with the drive windings oriented perpendicular to the longest dimension of the sample.

Sensitivity to carbide content in steels was also demonstrated for both single sense element sensors for spot inspections and for MWM-Arrays for scanning wide areas. For these measurements, sample sets A and B had two different carbide contents. FIG. 22 and FIG. 23 show the result of a single element (FIG. 1) permeability measurement at the center and on the top of the samples. The measurements covered a broad frequency range (31.8 kHz to 1.26 MHz) using a sensor approximately 0.5-in. by 0.5-in. in size and assumed electrical conductivity of 2 MS/m for the MUT. The permeability was measured with the drive windings parallel to the longest sample dimension in FIG. 22 and with the drive windings perpendicular to the longest sample dimension in FIG. 23. The samples were approximately 0.625-in. wide and 2.48-in. long, except for sample A4, which was only 2.2-in. long. Across the entire frequency range there is a distinct separation between the sample sets for both sensor orientations, indicating that the different carbide contents between the samples can be separated.

Figure 24:
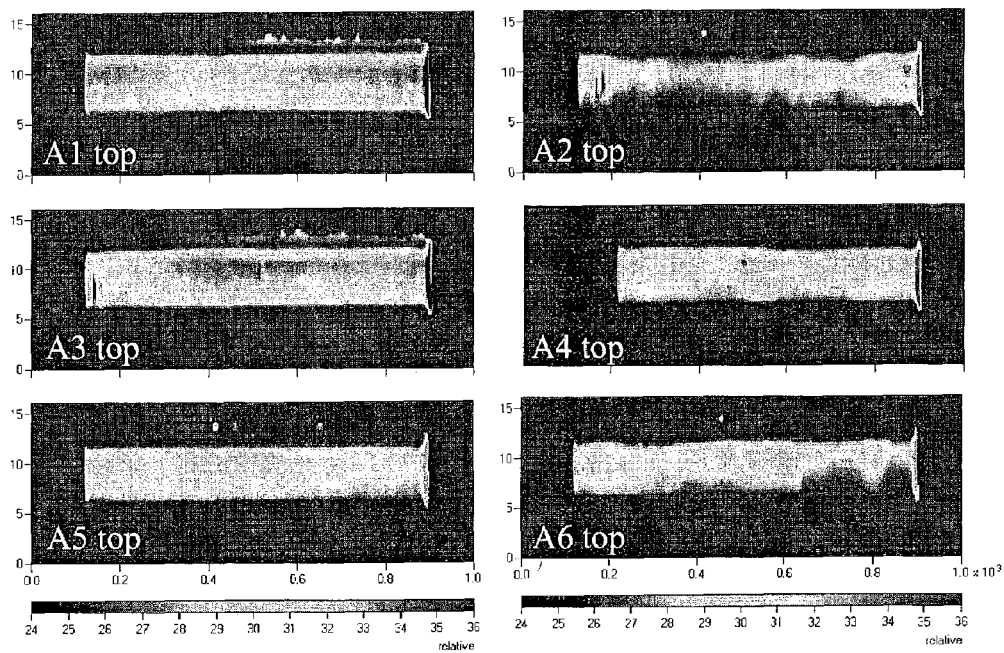
FIG. 24 illustrates a set of permeability images obtained from MWM-Array longitudinal scans over the tops of set A samples.
Figure 25:
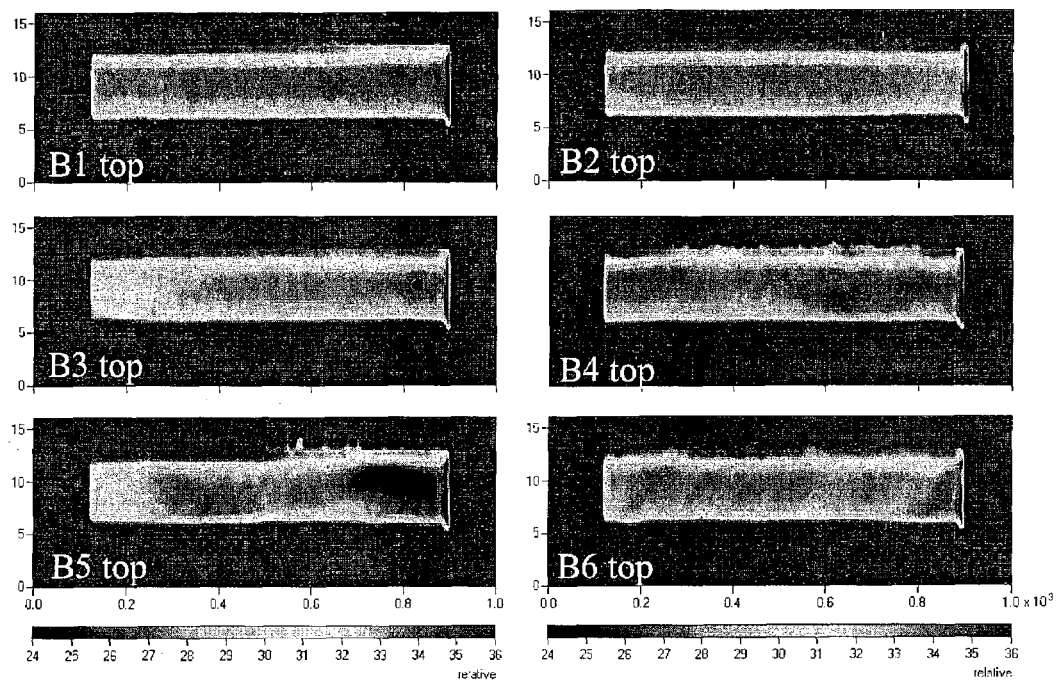
FIG. 25 illustrates a set of permeability images obtained from MWM-Array longitudinal scans over the tops of set B samples.
Figure 26:
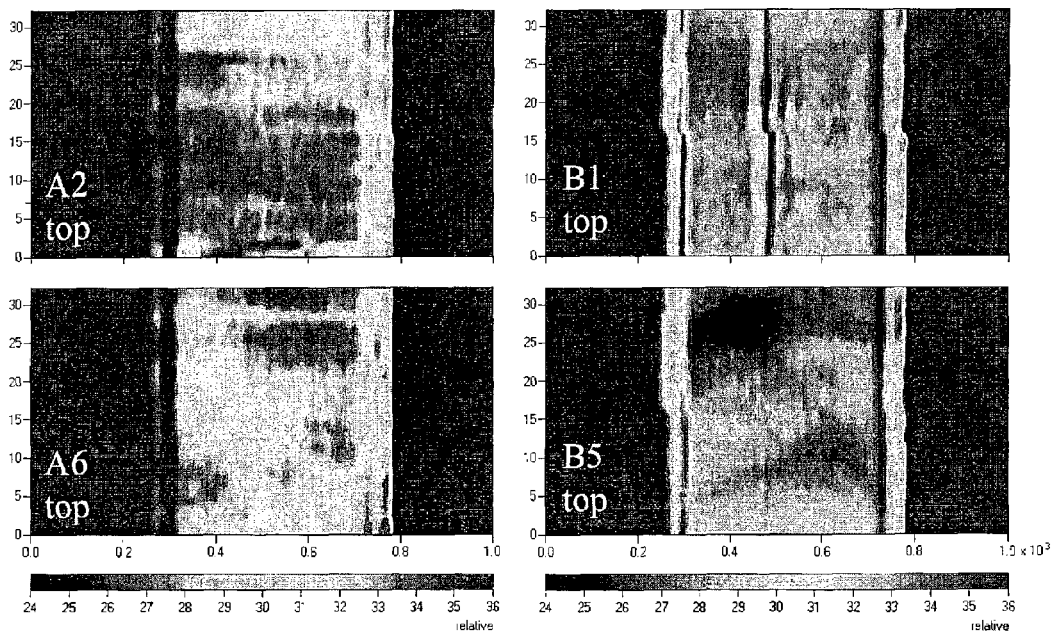
FIG. 26 illustrates a set of permeability images obtained from MWM-Array transverse scans over the tops of several samples.

Similar to FIG. 19 through FIG. 21 for the grinding burn samples, images were also taken of the samples with different carbide content. FIG. 24 shows a set of images of longitudinal scans over the top of samples in set A. FIG. 25 shows a set of images of longitudinal scans over the top of samples in set B. FIG. 26 shows a set of images of transverse scans over several of the samples. These images show that the magnetic permeability is much more uniform over the sample surface for the set B samples and the differences in the permeability are consistent with the permeability measured with a single sensing element so that the different carbide contents can also be separated using response images. Thus, the combination of images acquired in two orientations and multiple frequency responses from bi-directional MWM measurements of the effective magnetic permeability have the capability to separate the various effects of carbide content, grinding burns, and residual stresses.

Figure 27:
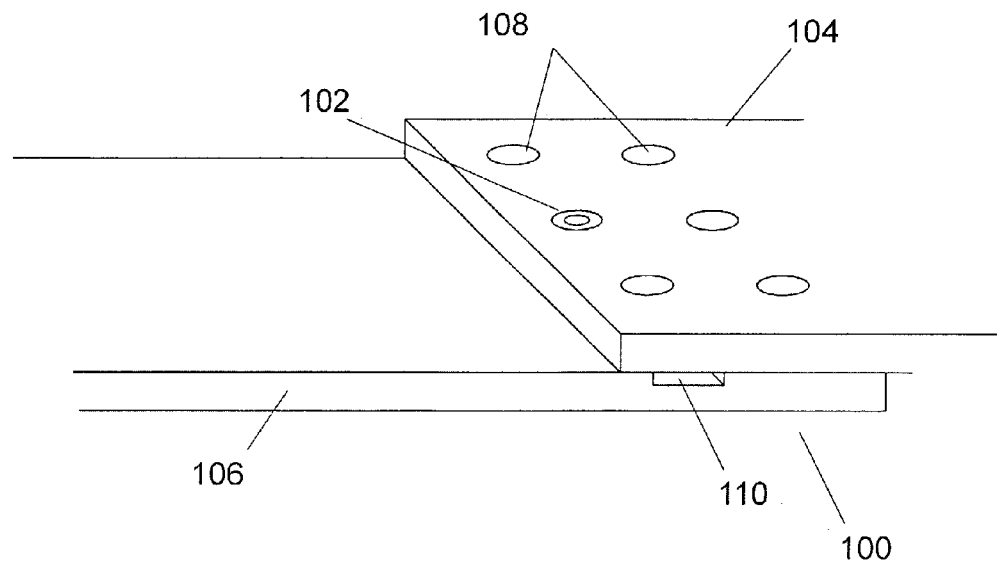
FIG. 27 illustrates an illustration of a lap joint.
Figure 28:
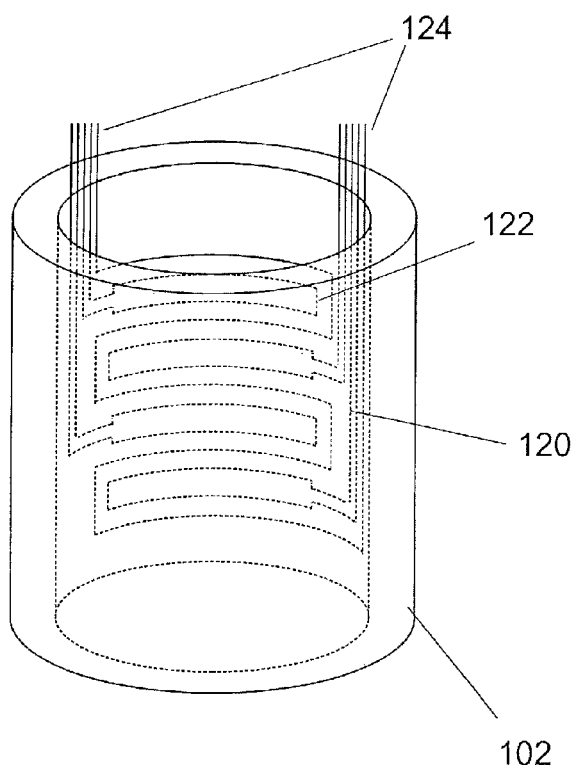
FIG. 28 illustrates an illustration of an MWM-Array inside a hollow fastener.

Another aspect of this invention is the use of hollow fasteners as load sensors in fatigue test articles and structures. This type of fastener may be used, for example, in structures where a sealant or lubricant needs to be injected. A schematic of a hollow fastener 102 in a lap joint 100 is shown in FIG. 27. The lap joint 100 between an upper panel 104 and lower panel 106 uses fasteners 108 to join the panels. A groove 110 may be present for providing a seal between the panels. The concept for monitoring the properties of the hollow fastener 102, shown in FIG. 28, is to mount an eddy-current sensor array 120 inside the fastener and to monitor changes in the fastener material properties as the load and stress distribution changes. For example, one or more property based parameters that relate to stresses can be measured. The use of a sensor array that has multiple sensing elements 122 with individual sensing element leads 124 permits the properties along the length of the fastener and/or around the circumference of the fastener to be monitored. In one embodiment, one parameter can be permeability in the axial direction and the other parameter can be permeability in the circumferential direction. Then, permeability changes can be related to stresses in the fasteners.

Example sensor arrays are the MWM-Arrays shown in FIG. 2 through FIG. 4, although other array formats can also be used, such as those described in U.S. patent application Ser. Nos. 09/666,879 and 09/666,524. These applications also describe using a magnetic material in combination with the sensor as a load cell and adjusting the sensitivity of the response through the selection of the material type and dimensions of the fastener as well as sensor and measurement parameters. Preferably, the fastener would be high strength steel in which the magnetic permeability varies with the typical stress levels applied to the fastener. This is also described in U.S. Provisional Application No. 60/382,447, filed May 21, 2002, the entire teachings of which are hereby incorporated by reference. Alternatively, if the changes in the stress distribution occur relatively slowly, periodic measurement of the stress distribution can be performed. This can be accomplished with occasional measurements with an MWM-Array that has been mounted to the inner surface of the fastener or by scanning eddy-current sensing arrays over the inner surface to provide a complete mapping of the material properties over the entire surface. In addition, measurements in multiple orientations, preferably two orthogonal orientations, can be performed to determine anisotropic material property variations associated with changes in stresses in the fasteners and can be determined with directional eddy-current sensor arrays. The MWM-Array is one such example as the sensing elements respond preferentially to the magnetic permeability oriented perpendicular to the extended segments comprising the primary winding.

Conventional eddy-current designs are not ideal for permanent mounting. Conventional eddy-current techniques require varying the proximity of the sensor (or lift-off) to the test material or reference part by rocking the sensor back and forth or scanning across a surface to configure the equipment settings and display. For example, for crack detection the lift-off variations are generally displayed as a horizontal line, running from right to left, so that cracks or other material property variations appear on the vertical axis. Affixing or mounting the sensors against a test surface precludes this calibration routine. The probe-to-probe variability of conventional eddy-current sensors prevents calibrating with one sensor and then reconnecting the instrumentation to a second (e.g., mounted) sensor for the test material measurements. These shortcomings are overcome with conformable eddy-current sensors that provide absolute property measurements and are reproduced reliably using micro-fabrication techniques. Calibrations can also be performed with duplicate spatially periodic field sensors using the response in air or on reference parts prior to making the connection with the surface mounted sensor. The capability to characterize fatigue damage in structural materials, along with the continuous monitoring of crack initiation and growth, has been demonstrated, as described in U.S. patnet application Ser. Nos. 09/666,879, 09/666,524, and 10/102,620. This inspection capability is suitable for on-line fatigue tests for coupons and complex components, as well as for monitoring of difficult-to-access locations on both military and commercial aircraft.

Figure 31:
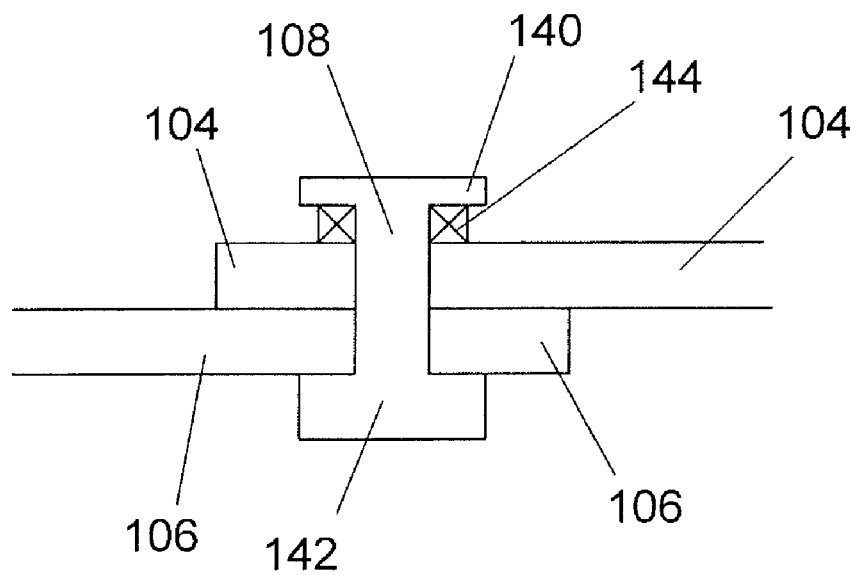
FIG. 31 illustrates an illustration of a single coil around the head of a fastener for stress monitoring.
Figure 32:
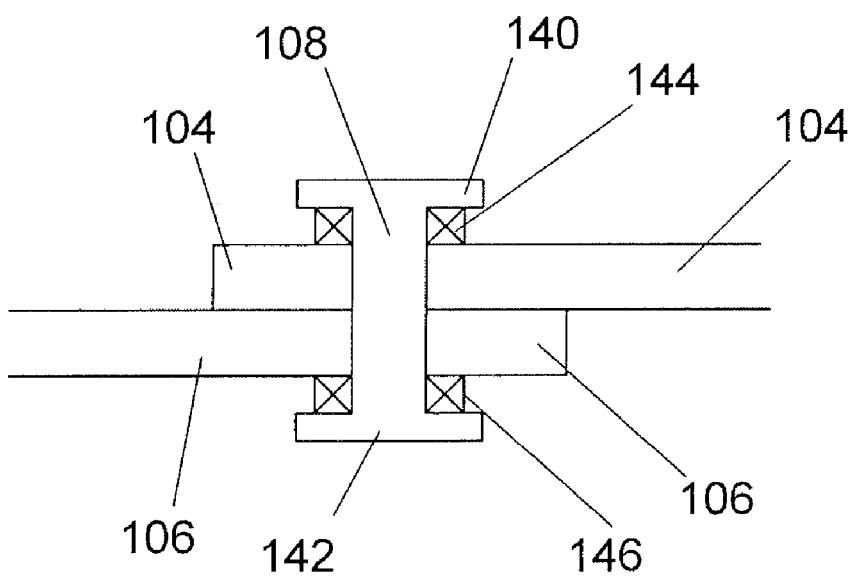
FIG. 32 illustrates an illustration of coils around the head and bottom of a fastener for stress monitoring.

If a multiple turn eddy-current sensing coil is well characterized, then it can be mounted to provide a measurement of the average stress in a fastener. One such example is shown in FIG. 31, where a coil 144 is mounted beneath the head 140 of a fastener 108. The bottom of the fastener 142 then holds the joint between plates 104 and 106 in place. When the fastener is made out of a magnetizable material, such as a steel, the self-inductance of the coil will reflect the stress and loading on the joint. Of course the head of the fastener is in a low-stress zone, and larger stresses are expected in the central region between the plates. If access to both sides of the joint is allowed, then it is preferable to add a second coil 146 onto the bottom of the fastener as well, as indicated in FIG. 32. Then, driving one coil and measuring the response on the second coil essentially creates a magnetic circuit and appreciable coupling can occur when the fastener is a magnetic material. As the stresses in the fastener vary, this affects the magnetic permeability and the response on the pickup or sense coil. This response is spatially averaged over the length of the fastener. Note that the coils can be larger or smaller than the head or bottom of the fastener, but smaller is preferred as more of the magnetic flux will then be linked into the magnetic material of the fastener.

Another aspect of this invention relates to the application of a stress-sensitive material to a test material and monitoring the properties of this stress-sensitive material to infer the stress distribution or mechanical load on the test article. The stress sensitive material could be a magnetic material in which the magnetic permeability changes significantly with stress, as illustrated in FIG. 13. An alternative stress-sensitive material is one whose electrical conductivity changes significantly with stress. This material could be nonmagnetic. In general, according to the literature on strain gages, metals typically have a gage factor reflecting change in resistance per unit strain of between 2 and 4. Representative values are listed in Table 1. Preferable materials for nonmagnetic stress-sensitive materials are platinum and platinum alloys because of the relatively large gage factors. It should be noted that conductivity variation with strain tends to become nonlinear for large strains and the listed gage factors are most applicable to situations of low strains. The choice of the stress-sensitive material can therefore depend on the strains anticipated for the inspection.

TABLE 1

Gage factors for stress-sensitive conducting materials.

| Material | Composition | Gage Factor |
| --- | --- | --- |
| Platinum | 100% Pt | 6.1 |
| Platinum-Iridium | 95% Pt, 5% Jr | 5.1 |
| Platinum-Tungsten | 92% Pt, 8% W | 4.0 |
| Isoelastic | 55.5% Fe, 36% Ni, 8% Cr, 0.5% Mo | 3.6 |
| Karma | 74% Ni, 20% Cr, 3% Al, 3% Fe | 2.4 |
| Constantan | 55% Cu, 45% Ni | 2.0 |
| Nichrome | 80% Ni, 20% Cu | 2.0 |
| Monel | 67% Ni, 33% Cu | 1.9 |
| Manganin | 84% Cu, 12% Mn, 4% Ni | 0.47 |
| Nickel | 100% Ni | −12.1 |

Figure 29:
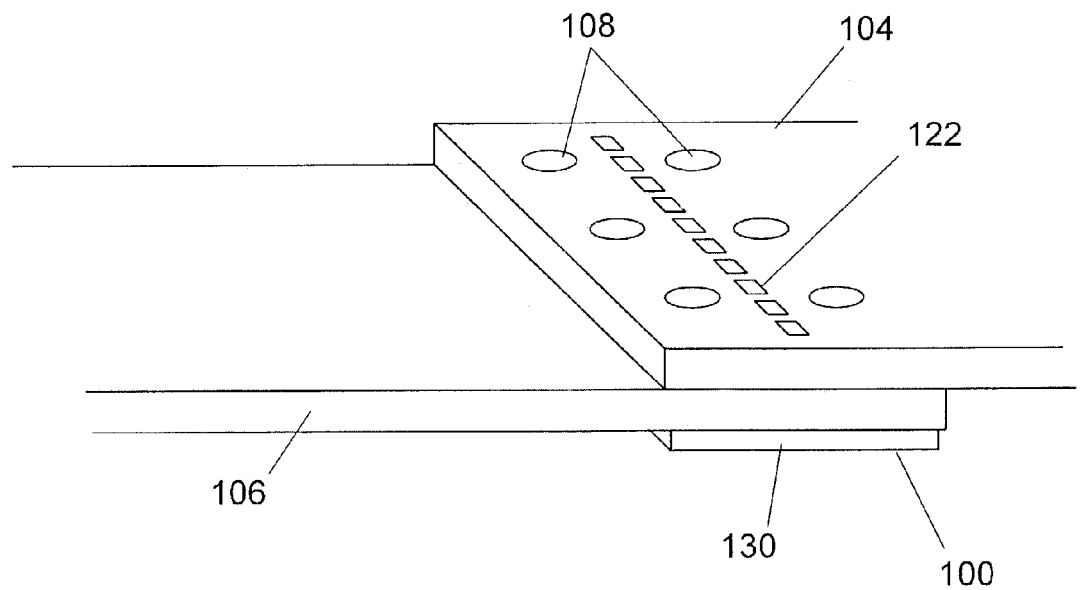
FIG. 29 illustrates an illustration of a lap joint with a stress-sensitive material and a sensor array.
Figure 30:
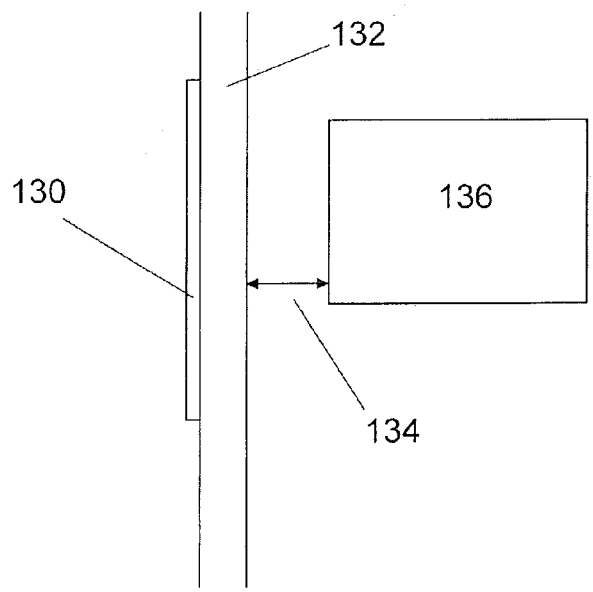
FIG. 30 illustrates an illustration of a non-contact measurement of a stress-sensitive material.

Monitoring the properties of a stress-sensitive material attached to a test material is most useful in situations where direct nondestructive measurements of the stresses in the test material are relatively difficult, such as in aluminum with eddy-current sensors. In contrast, monitoring the permeability changes of a layer of magnetic material or electrical conductivity changes of a layer of stress-sensitive non-magnetic material integrally attached to the test article can offer substantially greater sensitivity. The properties of the attached layer material can be monitored using a permanently mounted sensor or with a scanning sensor array to create images of the stress distribution. An illustration of this approach is given in FIG. 29, where the stress-sensitive material 130 is affixed to the back of the lap joint 100. The sensing elements 122 are shown in a linear array, but they could also be distributed among and around the fasteners as well. In this case, the drive winding is not shown. The measurements can also be performed in a non-contact fashion, as shown in FIG. 30, where an air gap 134 is maintained between the sensor or sensor array 136 and the test material 132. In both FIG. 29 and FIG. 30, the magnetic fields generated by the eddy-current sensor are projected through the test material so that the remote fields interact with the attached stress-sensitive layer and the sensor and attached layer material effectively operate as a load cell.

The sensitivity of this measurement approach is affected by the electrical and geometric properties of the stress-sensitive layer attached to the test material. The material should be selected so that the permeability or conductivity change for an anticipated stress level is detectable with the sensor and instrumentation. Furthermore, the material should be relatively thin to better reflect the stress distribution of the test material. However, it should also be thick enough to provide a measurable signal with the sensor or sensor array. Selection of the thickness of the layer must therefore balance these competing effects. The magnetic or non-magnetic stress-sensitive material can also be applied to the surface of the test material near the sensor.

The properties of the stress-sensitive material and even the base material itself that the coating is applied to can be obtained from multiple parameter estimation approaches. The use of multiple frequencies allows more than two parameters to be estimated. As an example, three, four and five parameter estimation routines have been developed for determining the properties of coatings, such as MCrAlY coatings used on turbine blades and vanes. As described in more detail in the DOE Phase II proposal "Intelligent Probes for Enhanced Non-Destructive Determination of Degradation in Hot-Gas-Path Components," a four parameter estimation routine is used for determining the coating electrical conductivity and thickness, the sensor lift-off, and the substrate electrical conductivity for nonmagnetizable materials. A five parameter algorithm that allows determination of an additional parameter, e.g., magnetic permeability when one of the layers is magnetizable is also described. Clearly, this multiple parameter estimation approach can be applied to different combinations of electrical and geometric properties for the various layers.

Figure 39:
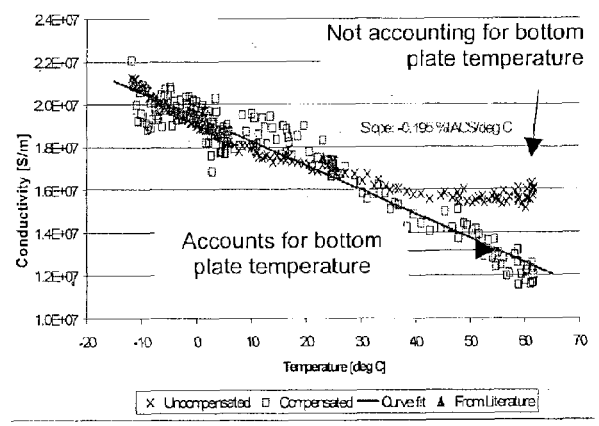
FIG. 39 illustrates a schematic for remotely monitoring the temperature of a plate.

As another alternative embodiments, in addition to inductive coils, other types of sensing elements, such as Hall effect sensors, magnetoresistive sensors, SQUIDS, and giant magnetoresistive (GMR) sensors, can also be used for the measurements. The use of GMR sensors for characterization of materials is described in more detail in U.S. patent application Ser. No 10/045,650. One example application using a GMR sensor is for monitoring properties through intermediate layers of metal. In this case, the absolute electrical properties are measured through thick metal plates and then related to other physical properties of interest. Here, a low frequency (100 Hz) measurement was used to remotely monitor the temperature dependent conductivity variation of an aluminum plate through a 0.25-in. thick aluminum plate. The thickness of the upper plate (remote from the sensor), the conductivity and thickness of the bottom plate (near the sensor), as well as its lift-off (proximity) from the sensor windings, are incorporated in the model used to generate the appropriate measurement grids. The two unknown properties are the conductivity of the upper plate and the thickness of the thermally insulating nonconducting spacer between the two plates, which also varied significantly with the temperature of the upper plate. The ability to measure the two unknown parameters independently is demonstrated by taking measurements at room temperature with spacers of varying thickness and demonstrating that the data follow a constant-conductivity line in the grid. To verify and record the actual plate temperatures, thermocouples were attached to both metal plates. The top plate was initially chilled and then gradually heated with a hot air gun. The data of FIG. 39 shows that both the conductivity and spacer thickness are affected by the plate temperature.

In this experiment, the temperature of the bottom plate also increased, despite the thermal insulation. Ignoring this effect yields the plot in FIG. 39 with cross symbols. To compensate for the temperature variation of the bottom plate, data were also taken at 10 kHz simultaneously with the 100 Hz measurement. At this higher frequency the bottom plate appears infinitely thick since it is more than several skindepths thick and a simple conductivity/lift-off grid can be used to independently determine the bottom plate's conductivity. Once this value is obtained, it can be used in the estimation of the upper plate conductivity via a three-dimensional measurement grid, called a grid lattice. Using this method, the data shown with squares in FIG. 39 are obtained. As expected, it follows a linear relationship.

Figure 40:
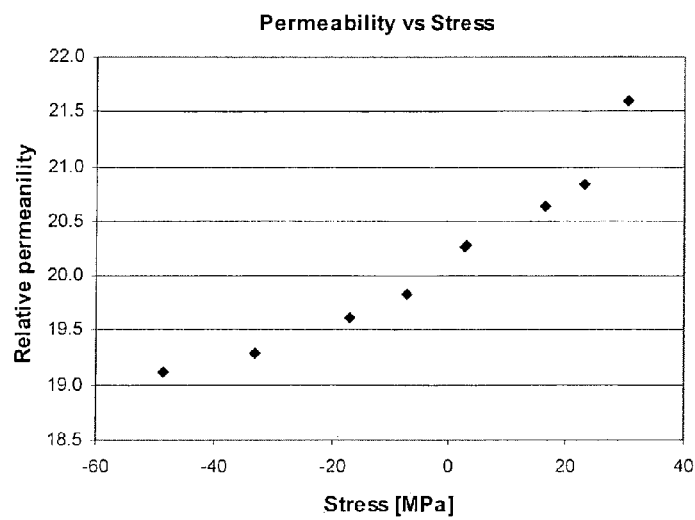
FIG. 40 illustrates the top plate conductivity as a function of temperature with and without compensation for changes in the conductivity of the bottom plate, which is between the top plate and the sensor.
Figure 41:
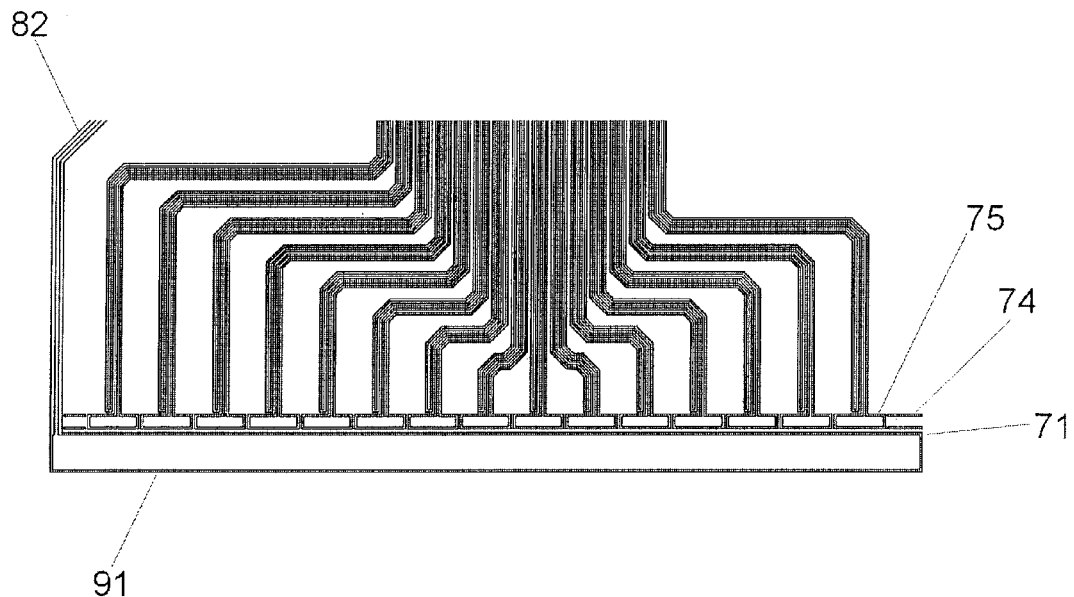
FIG. 41 illustrates a plot of the top plate relative penneability as a function of the top plate strain at varying levels of applied stress.

Another example measurement with a GMR sensor is to monitor stress. In this case, measurements were performed on a hidden steel layer in a thick structure. A 1.4 mm thick steel plate was suspended over a 6.7 mm Al 6061 plate using a 3 mm thick spacer located in the center. A 5 kg weight was used to keep the center part of the plate from moving. The measurement grid used in this case was a permeability/spacer thickness grid. The spacer thickness was one of the unknowns since it varied as the steel plate was deformed under the applied force. Zero stress is registered when the plate is placed on a flat surface. The measured relative permeability as a function of the applied stress at the bottom of the plate are shown in FIG. 40. This illustrates the capability to measure stress (or strain) on a buried steel layer through relatively thick intermediate aluminum and insulating layers.

While the inventions have been particularly shown and described with reference to preferred embodiments thereof, it will be understood to those skilled in the art that various changes in form and details may be made therein without departing from the spirit and scope of the invention as defined by the appended claims.

REFERENCES INCORPORATED BY REFERENCE IN THEIR ENTIRETY

Auld, B. A. and Moulder, J. C. (1999), "Review of Advances in Quantitative Eddy-Current Nondestructive Evaluation," Journal of Nondestructive Evaluation, vol. 18, No. 1.
Bozorth, R. M., Ferromagnetism, IEEE Press, 1978.
Bray, D. E., ed., Residual Stress Measurement and General Nondestructive Evaluation, PVP-Vol. 429, ASME Pressure Vessels and Piping Conference, Atlanta, Ga., ASME, 2001.
Hydrogen in Metals, Proceedings of the Second Japan Institute of Metals, International Symposium, 1979.
Interrante, C. and Pressouyre, G. "Current Solutions to Hydrogen Problems in Steels," Proceedings of the First International Conference, ASM, 1982.
Lawrence, S. C. "Hydrogen Detection Gage," Hydrogen Embrittlement Testing, ASTM STP 543, 1974, pp.83-105.

The Following References are also Incorporated Herein by Reference in their Entirety.

1. Navy Phase I Proposal, titled "Wireless Communications with Electromagnetic Sensor Networks for Nondestructive Evaluation," Topic #N01-174, dated Aug. 13, 2001.
2. Air Force Phase I Proposal, titled "Three-Dimensional Magnetic Imaging of Damage in Multiple Layer Aircraft Structures," Topic #AF02-281, dated Jan. 14, 2002.
3. DOE Phase II Proposal, titled "Intelligent Probes for Enhanced Non-Destructive Determination of Degradation in Hot-Gas-Path Components," Topic #44c, dated Mar. 23, 2002.
4. Air Force Phase II Proposal, titled "Detection and Imaging of Damage, Including Hydrogen Embrittlement Effects in Landing Gear and Other High-Strength Steel Components," Topic #AF01-308, dated Apr. 9, 2002.
5. Strategic Environmental Research and Development Program Proposal, titled "High Resolution Inductive Sensor Arrays for UXO Detection, Identification and Clutter Suppression,", SON #UXSON-02-03, dated Apr. 17, 2002.
6. NASA Phase II Proposal, titled "Shaped Field Giant Magnetoresisitive Sensor Arrays for Materials Testing," Topic #01-II A1.05-8767, dated May 2, 2002
7. Navy Phase I Proposal, titled "Observability Enhancement and Uncertainty Mitigation for Engine Rotating Component PHM," Topic #N02-188, dated Aug. 14, 2002.
8. NASA Phase I Proposal, titled "Non-Destructive Evaluation, Health Monitoring and Life Determination of Aerospace Vehicles/Systems," Topic #02-H5.03-8767, dated Aug. 21, 2002.
9. Final Report submitted to FAA, titled "Crack Detection Capability Comparison of JENTEK MWM-Array and GE Eddy-current Sensors on Titanium ENSIP Plates", dated Sep. 28, 2001, Contract #DTFA03-00-C-00026, option 2 CLIN006 and 006a.
10. Final Report submitted to FAA, titled "Aircraft Hidden Damage Detection and Assessment with Conformable Eddy-current Arrays," dated March 29, 2002.
11. Final Report submitted to NASA, titled "Shaped Field Giant Magnetoresisitive Sensor Arrays for Materials Testing," dated May 3, 2002.
12. Final Report submitted to Air Force, titled "Detection and Imaging of Damage, Including Hydrogen Embrittlement Effects in Landing Gear and Other High-Strength Steel Components," dated Jul. 3, 2002.
13. Final Report submitted to Navy, titled "Wireless Communications with Electromagnetic Sensor Networks for Nondestructive Evaluation," dated Jul. 15, 2002.
14. Final Report titled "Portable Accumulated Fatigue Damage Inspection System Using Permanently Mounted and Wide-Area Imaging MWM-Arrays," dated Aug. 23, 2002.
15. Technical paper titled "MWM-Eddy-Current Arrays for Crack Initiation and Growth Monitoring," submitted to International Journal of Fatigue, from the International Conference on Fatigue Damage of Structural Materials IV, Hyannis, Mass, 2002.Technical paper titled "Conformable Eddy-Current Sensors and Arrays for Fleet-wide Gas Turbine Component Quality Assessment," published in ASME Journal of Engineering for Gas Turbines and Power, Volume 124, No. 4, pp 904-909; October 2002.
16. Technical paper titled "Residual and Applied Stress Estimation from Directional Magnetic Permeability Measurements with MWM Sensors," published in ASME Journal of Pressure Vessel Technology, Volume 124, pp 375-381; August 2002.
17. Technical paper titled "Fatigue and Stress Monitoring Using Scanning and Permanently Mounted MWM-Arrays," presented at 29th Annual Review of Progress in QNDE; Bellingham, Wash.; July 2002.
18. Technical paper titled "Absolute Electrical Property Imaging using High Resolution Inductive, Magnetoresistive and Capacitive Sensor Arrays for Materials Characterization," presented at 11$^{th}$ International Symposium on Nondestructive Characterization of Materials, Berlin, Germany; June, 2002.
19. Technical paper titled "Application of MWM® Eddy-Current Technology during Production of Coated Gas Turbine Components," presented at 11$^{th}$ International Symposium on Nondestructive Characterization of Materials, Berlin, Germany; June 2002.
20. Technical paper titled "Friction Stir Weld Inspection through Conductivity Imaging using Shaped Field MWM$^{s}$-Arrays," presented at ASM Trends in Welding Conference, Callaway Gardens, Ga.; April 2002.
21. Technical paper and presentation slides, titled "MWM-Array Characterization and Imaging of Combustion Turbine Components," presented at EPRI International Conference on Advances in Life Assessment and Optimization of Fossil Power Plants, Orlando, Fla.; March 2002.
22. Technical paper titled "Surface Mounted and Scanning Periodic Field Eddy-Current Sensors for Structural Health Monitoring", presented at the IEEE Aerospace Conference, March 2002.
23. Presentation slides titled "Corrosion Detection and Prioritization Using Scanning and Permanently Mountable MWM Eddy-Current Arrays," U.S. Army Corrosion Summit, March 2002.
24. Technical paper and presentation slides titled "Shaped-Field Eddy-current Sensors and Arrays", SPIE 7$^{th}$ Annual International Symposium: NDE for Health Monitoring and Diagnostics, March 2002.
25. Technical paper titled "Corrosion Detection and Prioritization Using Scanning and Permanently Mounted MWM Eddy-Current Arrays", Tri-Service Corrosion Conference, January 2002

26. Technical presentation slides "Condition Assessment of Engine Component Materials Using MWM-Eddy-current Sensors," ASNT Fall Conference, Columbus, Ohio; October 2001.
27. Technical paper titled "Flexible Eddy-current Sensors and Scanning Arrays for Inspection of Steel and Alloy Components," 7$^{th}$ EPRI Steam Turbine/Generator Workshop and Vendor Exposition, Baltimore, Md.; August 2001.
28. Technical paper titled "Applications for Conformable Eddy-current Sensors including High Resolution and Deep Penetration Sensor Arrays in Manufacturing and Power Generation," ASME 7$^{th}$ NDE Topical Conference, San Antonio, Tex.; 2001.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for monitoring the stress on a structural article, said method comprising:
    affixing a stress-sensitive material layer to the structural article, the material having a stress sensitive electrical property that varies with stress;
    simultaneously, using an electromagnetic sensor, measuring said stress sensitive electrical property and a second property that does not vary significantly with stress;
    correcting for variations in the stress sensitive electrical property, that are not due to stress, with the second property to provide a corrected stress sensitive physical property; and
    monitoring the stress on the structural article by relating said corrected stress sensitive electrical property to the stress on the article.

2. The method as claimed in claim 1, wherein the electrical property and the second property are measured with one eddy-current sensor.

3. The method as claimed in claim 2, wherein the sensor is an eddy-current sensor array.

4. The method as claimed in claim 3, wherein the sensor array is scanned over the surface of the article.

5. The method as claimed in claim 1, wherein the sensor array is inductive and is mounted to the surface of the article.

6. The method as claimed in claim 1, wherein the stress-sensitive material is steel with a magnetic relative permeability greater than one.

7. The method as claimed in claim 1, wherein the stress-sensitive material is nonmagnetic metal.

8. The method as claimed in claim 1, wherein the electrical property is the magnetic permeability.

9. The method as claimed in claim 1, wherein the electrical property is the electrical conductivity.

10. The method as claimed in claim 1, wherein the stress-sensitive material is mounted at a hidden surface, on the opposite surface from the sensor.

11. The method as claimed in claim 1, wherein the stress-sensitive non-magnetic material is mounted on top of the article, between the article and the sensor.

12. The method as claimed in claim 1 wherein the sensor is not in contact with surface of the article.

13. The method as claimed in claim 1 wherein the sensor contains a magnetoresistive sensor.

14. The method as claimed in claim 1 wherein the second property is sensor proximity to the stress-sensitive material.

15. The method as claimed in claim 1 wherein the second property is sensor proximity to the article.

16. The method as claimed in claim 1 wherein the second property is the stress-sensitive material thickness.

17. The method as claimed in claim 1, wherein the second property is electrical conductivity.

18. The method as claimed in claim 1 wherein the second property is used to improve the relation between the electrical property and stress.

19. The method as claimed in claim 18 wherein the second property is used to correct the measurement of the electrical property.

20. The method as claimed in claim 18 further comprising: verifying that the second property does not vary with stress.

21. The method as claimed in claim 1 wherein a precomputed database of sensor responses is used to simultaneous measure the stress sensitive electrical property and the second property.

22. The method as claimed in claim 1 wherein the stress sensitive electrical property is magnetic permeability and the second property is electrical conductivity, the method further including:
    measuring temperature effects with the electrical conductivity; and
    correcting for variations in the permeability, that are not caused by stress, with the temperature effects.

23. A method for monitoring the stress on a structural article, said method comprising:
    affixing a stress-sensitive material layer to the structural article, the material having a stress sensitive physical property that varies with stress;
    simultaneously, using an electromagnetic sensor, measuring said stress sensitive physical property and a second property that does not vary significantly with stress the sensor, the sensor being distinct from the stress-sensitive layer;
    correcting for variations in the stress sensitive property, that are not due to stress, with the second property to provide a corrected stress sensitive property; and
    monitoring the stress on the structural article by relating said corrected stress sensitive physical property to the stress on the article.

* * * * *